(12) United States Patent
Sohn et al.

(10) Patent No.: US 8,309,359 B2
(45) Date of Patent: Nov. 13, 2012

(54) ISOBARIC TAGS FOR ANALYTE DETECTION AND QUANTIFICATION

(75) Inventors: Chang Ho Sohn, Pasadena, CA (US); Jesse L. Beauchamp, La Canada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 121 days.

(21) Appl. No.: 13/007,513

(22) Filed: Jan. 14, 2011

(65) Prior Publication Data

US 2011/0207228 A1    Aug. 25, 2011

Related U.S. Application Data

(60) Provisional application No. 61/295,641, filed on Jan. 15, 2010.

(51) Int. Cl.
G01N 1/28 (2006.01)
G01N 27/00 (2006.01)
C07D 249/04 (2006.01)

(52) U.S. Cl. .............. 436/56; 436/17; 436/86; 436/96; 436/98; 436/106; 436/161; 436/173; 436/174; 252/408.1; 250/281; 250/282; 422/70; 422/430; 548/255

(58) Field of Classification Search .............. 436/8, 17, 436/56, 86, 96, 98, 106, 161, 173, 174; 252/408.1; 250/281, 282; 422/70, 430; 548/255

See application file for complete search history.

(56) References Cited

U.S. PATENT DOCUMENTS

| 7,294,456 | B2 | 11/2007 | Schmidt et al. |
| 7,799,576 | B2* | 9/2010 | Pappin et al. ................. 436/173 |
| 2004/0219685 | A1 | 11/2004 | Pappin et al. |
| 2005/0148087 | A1 | 7/2005 | Pappin et al. |
| 2006/0263293 | A1 | 11/2006 | Kolb et al. |
| 2008/0014642 | A1 | 1/2008 | Purkayastha |
| 2009/0002703 | A1 | 1/2009 | Parman |
| 2010/0129842 | A1* | 5/2010 | Pappin et al. ................... 435/18 |
| 2010/0190183 | A1 | 7/2010 | Hoffmann et al. |
| 2010/0311175 | A1* | 12/2010 | Yan et al. ........................ 436/71 |
| 2011/0003395 | A1* | 1/2011 | Dey et al. ........................ 436/98 |
| 2011/0028685 | A1* | 2/2011 | Purkayastha et al. ......... 530/300 |
| 2011/0143951 | A1* | 6/2011 | Thompson ........................ 506/7 |

FOREIGN PATENT DOCUMENTS

EP    1 275 004 B1    6/2007

OTHER PUBLICATIONS

Dayon et al. Analytical Chemistry, vol. 80, No. 8, Apr. 15, 2008, pp. 2921-2931.*

Köcher, et al., "*High Precision Quantitative Proteomics Using iTRAQ on an LTQ Orbitrap: A New Mass Spectrometric Method Combining the Benefits of All*", Journal of Proteome Research, vol. 8, 2009, pp. 4743-4752.

(Continued)

*Primary Examiner* — Maureen Wallenhorst
(74) *Attorney, Agent, or Firm* — Christie, Parker & Hale, LLP

(57) ABSTRACT

Isobaric reagents for labeling analytes are provided. The isobaric reagents have facile design and synthesis that allows for differential labeling of an unlimited number of analyte samples.

27 Claims, 14 Drawing Sheets

OTHER PUBLICATIONS

International Search Report and Written Opinion dated Sep. 28, 2011 for corresponding PCT Application No. PCT/US2011/021434 (9 sheets).

Domon, B. & Aebersold, R. Review—Mass spectrometry and protein analysis. *Science* 312, pp. 212-217 (2006).

Service, R.F. Proteomics: Proteomics Ponders Prime Time, New Focus, *Science* 321, pp. 1758-1761 Sep. 26, 2008.

de Godoy, L.M.F. et al. Comprehensive mass-spectrometry-based proteome quantification of haploid versus diploid yeast. *Nature* 455, pp. 1251-1254 (2008).

Ong, S.-E. & Mann, M. Mass spectrometry-based proteomics turns quantitative. *Nat Chem Biol* 1, pp. 252-262 (2005).

Gstaiger, M. & Aebersold, R. Applying mass spectrometry-based proteomics to genetics, genomics and network biology. *Nat. Rev. Genet.* 10, pp. 617-627 (2009).

Gygi, S.P. et al. Quantitative analysis of complex protein mixtures using isotope-coded affinity tags. *Nat. Biotechnol.* 17, pp. 994-999 (1999).

Ong, S.-E. et al. Stable Isotope Labeling by Amino Acids in Cell Culture, SILAC, as a Simple and Accurate Approach to Expression Proteomics. *Mol Cell Proteomics* 1, pp. 376-386 (2002).

Thompson, A. et al. Tandem Mass Tags: A Novel Quantification Strategy for Comparative Analysis of Complex Protein Mixtures by MS/MS. *Anal. Chem.* 75, pp. 1895-1904 (2003).

Dayon, L. et al. Relative Quantification of Proteins in Human Cerebrospinal Fluids by MS/MS Using 6-Plex Isobaric Tags. *Anal. Chem.* 80, pp. 2921-2931 (2008).

Ross, P.L. et al. Multiplexed Protein Quantitation in *Saccharomyces cerevisiae* Using Amine-reactive Isobaric Tagging Reagents. *Mol Cell Proteomics* 3, pp. 1154-1169 (2004).

Choe, L. et al. 8-Plex quantitation of changes in cerebrospinal fluid protein expression in subjects undergoing intravenous immunoglobulin treatment for Alzheimer's disease, *Proteomics* 7, pp. 3651-3660 (2007).

Seo, J. et al. Mass-balanced $^1$H/$^2$H isotope dipeptide tag for simultaneous protein quantitation and identification. *Anal. Chem.* 80, pp. 6145-6153 (2008).

Tagwerker, C. et al. A tandem affinity tag for two-step purification under fully denaturing conditions—Application in ubiquitin profiling and protein complex identification combined with in vivo crosslinking. *Mol. Cell. Proteomics* 5, pp. 737-748 (2006).

Cronan, J.E. Biotination of Proteins In Vivo—a Posttranslational Modification to Label, Purify, and Study Proteins. *Journal of Biological Chemistry* 265, pp. 10327-10333 (1990).

Kulman, J.D., Satake, M. & Harris, J.E. A versatile system for site-specific enzymatic biotinylation and regulated expression of proteins in cultured mammalian cells. *Protein Expr. Purif.* 52, pp. 320-328 (2007).

Alvarez, S.G. & Alvarez, M.T. A practical procedure for the synthesis of alkyl azides at ambient temperature in dimethyl sulfoxide in high purity and yield. *Synthesis*, pp. 413-414 (1997).

Kacprzak, K. Efficient one-pot synthesis of 1,2,3-triazoles from benzyl and alkyl halides. *Synlett*, pp. 943-946 (2005).

Bantscheff, M. et al. Robust and sensitive iTRAQ quantification on an LTQ orbitrap mass spectrometer. *Mol. Cell. Proteomics* 7, pp. 1702-1713 (2008).

Cox, J. & Mann, M. MaxQuant enables high peptide identification rates, individualized p.p.b.-range mass accuracies and proteome-wide protein quantification. *Nat. Biotechnol.* 26, pp. 1367-1372 (2008).

Hermanson, Greg T., (2008). "Bioconjugate Reagents," Bioconjugate Techniques, Part 2, pp. 1, 213-742, Academic Press, (New York).

Seiber, P., et al., Side-Chain Protection of Asparagine and Glutamine by Trityl. Application to solid-phase peptide synthesis. Innovation and Perspectives in Solid Phase Synthesis, Editor: Roger Epton, SPCC (UK) Ltd, Birmingham, 1990) pp. 577-583.

Morris HR, et al. (1981). "Fast atom bombardment: a new mass spectrometric method for peptide sequence analysis". Biochem. Biophys. Res. Commun. 101 (2): pp. 623-631.

Aebersold, R. et al., Mass Spectrometry in Proteomics. Chem. Rev. 101: pp. 269-295 (2001).

Mak, M. et al., Stability of Asp-Pro Bond Under High and Low Energy Collision Induced Dissociation Conditions in the Immunodominant Epitope Region of Herpes Simplex Virion Glycoprotein D, Rapid Commun. Mass Spectrom., 12: pp. 837-842) (1998).

Eng, J. et al., An Approach to Correlate Tandem Mass Spectral Data of Peptides with Amino Acid Sequences in a Protein Database, J. Am. Soc. Mass Spectrom., 5: pp. 976-989 (1994).

Perkins, D. et al., Probability-based protein identification by searching sequence databases using mass spectrometry data, Electrophoresis, 20: pp. 3551-3567 (1999).

Yates, J. R., Mass Spectrometry from Genomics to Proteomics, Trends, Genetics, 16: pp. 5-8 Jan. (2000).

Yates, J. R., Database searching using mass spectrometry data, Electrophoresis 19: pp. 893-900 (1998).

Rautenbach, M., et al., Solid Phase Synthesis of Peptides on Polyamide Resins at Elevated Temperatures. Innovation and Perspectives in Solid Phase Synthesis, Editor: Roger Epton, SPCC (UK) Ltd, Birmingham, 1990) pp. 547-550.

Zdravkovski, Z., The Role of Polymer Catalyst Structure on Conversion of Alcohols and Amines to Esters and Amides, Innovation and Perspectives in Solid Phase Synthesis, Editor: Roger Epton, SPCC (UK) Ltd, Birmingham, 1990) pp. 609-615.

Thermo Scientific Pierce Crosslinking Technical Handbook, Thermo Fisher Scientific, 2009, pp. 1-45.

\* cited by examiner

ISOBARIC TAGS FOR ANALYTE DETECTION AND QUANTIFICATION

CROSS-REFERENCE TO RELATED APPLICATION(S)

The present application claims priority to U.S. Provisional Application Ser. No. 61/295,641, filed Jan. 15, 2010, the entire contents of which are incorporated herein by reference.

STATEMENT REGARDING FEDERALLY SPONSORED RESEARCH OR DEVELOPMENT

The U.S. Government has certain rights in this invention pursuant to Grant No. CHE0416381 awarded by the National Science Foundation.

BACKGROUND

Isobaric chemical tags are tools used in mass spectrometry (MS)-based quantitative proteomics for labeling analytes in different samples to be quantified concurrently. Isobaric tags are usually a set of molecules with identical structures that consist of a reporter, a balancer, and a reactive group. Stable isotopes are incorporated at multiple positions so that the reporter region in each reagent of the set differs in mass, but the difference is compensated by a balancer, such that all tagged analytes (parent ion) have the same mass and appear as a single peak in the mass spectrum. However, after the parent ions are isolated and fragmented in a subsequent tandem mass spectrometry (MS/MS) measurement, a series of reporter ions are produced with differing masses, which allows for relative quantification of the parent ions or the relative abundance of the same analyte in different samples.

Isobaric tags offer two major advantages: 1) multiplex and high-throughput analysis of multiple samples; and 2) improved detection sensitivity because analytes from different samples contribute to the amplitude of a single peak. Two commercially available isobaric reagents are Tandem Mass Tag (TMT) from Thermo Scientific, and Isobaric Tag for Relative and Absolute Quantification (iTRAQ) from Applied Biosystems.

Despite the advantages of presently available isobaric tags, such as TMT and iTRAQ, these tags are limited to a total of 8 samples because the number of reporter ions are restricted by a limited structure having limited isotopic substitutions. These tags are also further limited by their high cost from tedious synthesis. Accordingly, isobaric tags having facile synthesis that allow for differential labeling of an unlimited number of samples are desired for quantifying analytes of interest.

SUMMARY

In one aspect of the present invention, a reagent for labeling an analyte is provided, the reagent represented by Formula I:

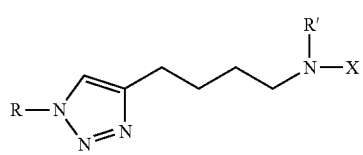

(I)

wherein:
R is a hydrocarbon group or a hydrocarbon group containing one or more heteroatoms;
R' is an isotopomer of R; and
X is a reactive group capable of coupling to the analyte.

In a second aspect of the invention, a kit including (m) number of reagents for labeling (m) number of analytes is provided, the kit including: a first reagent; and at least a second reagent, wherein the first reagent and the at least a second reagent are, independently represented by Formula I:

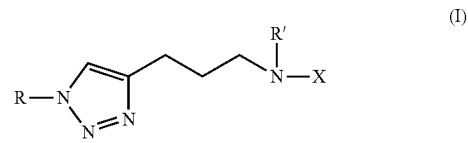

(I)

wherein:
R is a hydrocarbon group or a hydrocarbon group containing one or more heteroatoms;
R' is an isotopomer of R; and
X is a reactive group capable of coupling to the analytes,
wherein for each reagent, the sum of the mass of R and the mass of R' is constant, and wherein the mass of R of each reagent differs from the mass of every other R of the reagents in the kit, and the mass of R' of each reagent differs from the mass of every other R' of the reagents in the kit.

In a third aspect of the invention, a kit including (m) number of reagents for labeling (m) number of analytes is provided, the kit including: a first reagent; and at least a second reagent, wherein the first reagent and the at least a second reagent are, independently represented by Formula X:

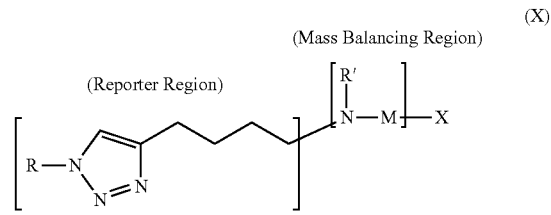

(X)

wherein:
R is a hydrocarbon group or a hydrocarbon group containing one or more heteroatoms;
R' is an isotopomer of R;
M is a hydrocarbon linker group; and
X is a reactive group capable of coupling to the analyte;
wherein for each reagent, the sum of the mass of the Reporter Region and the mass of Mass Balancing Region is constant, and wherein the mass of the Reporter Region of each reagent differs from the mass of every other Reporter Region of the reagents in the kit, and the mass of the Mass Balancing Region of each reagent differs from the mass of every other Mass Balancing Region of the reagents in the kit.

In a fourth aspect of the present invention, a method of detecting (m) number of analytes is provided, the method including: forming (m) number of labeled analytes by labeling the (m) number of analytes with the kit including (m) number of reagents of Formulas I or X above; the method including: separating the labeled analytes by chromatography; ionizing the separated, labeled analytes to obtain analyte ions; isolating the analyte ions; activating the isolated analyte ions to obtain a reporter ions; and detecting the mass of the reporter ions by tandem mass spectrometry.

DETAILED DESCRIPTION

Figure 1:
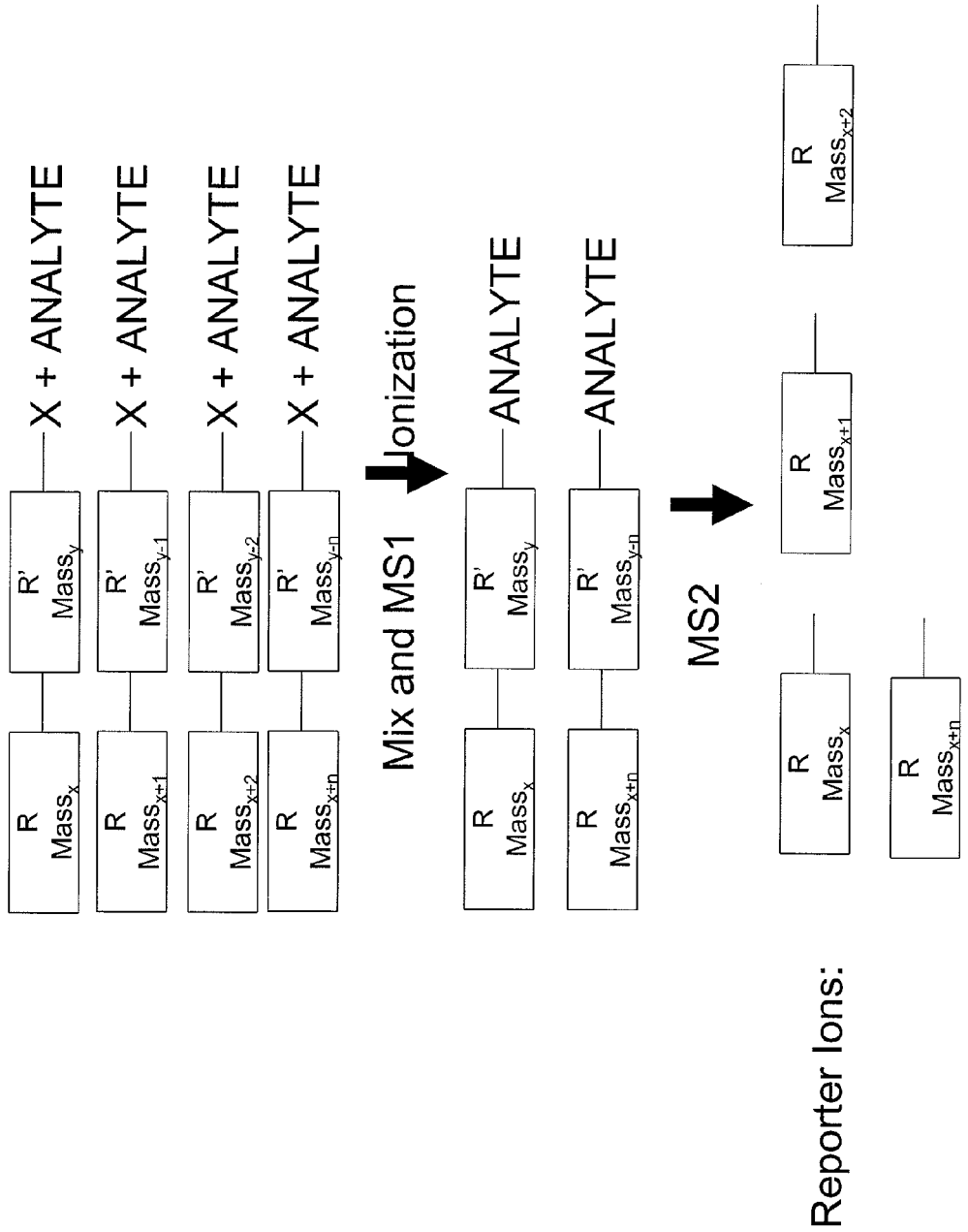
FIG. 1 is a schematic of isobaric reagents according to the present invention.

An isobaric chemical labeling reagent is provided for labeling analytes to be quantified. The isobaric chemical labeling reagent of the present invention is also referred to as an isobaric reagent and/or isobaric tag.

The isobaric reagent of the present invention provides for analyte labeling using a low energy fragmentation pathway that is triggered by a nucleophilic attack of a 1,2,3-triazole ring that connects a mass balance group (R'—NH) and a reporter ion group (R-1,2,3-triazole) (Formula I and Scheme I). In one embodiment, this advantageous nucleophilic reaction results in a stable (low energy) 5,6-membered ring reporter ion. And, because the nucleophilic reaction of the 1,2,3-triazole ring with the Cα of the protonated tertiary amine will occur with a variety of reporter side groups (R), the number of possible isobaric tags is practically unlimited. That is, the reporter side groups (R) can be synthesized to provide (n) number of atoms to allow for at least (n+1) number of distinct isobaric tags.

An analyte that is labeled with an isobaric tag of the present invention can be any analyte of interest. Non-limiting examples of analytes include peptides, proteins, nucleic acids, carbohydrates, lipids, steroids, and small molecules. Non-limiting examples of small molecules include dopamine, serotonin, metabolites, neurotransmitters, and other chemical messengers.

In one embodiment, an isobaric tag of the present invention has a generic structure represented by Formula I:

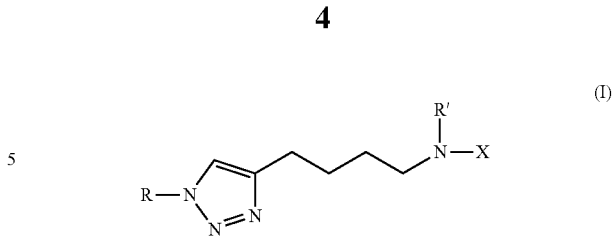

wherein, R is any hydrocarbon moiety which may include one or more heteroatoms of oxygen and/or nitrogen, as described herein; R' is an isotopomer of R; and X is a reactive group as described herein.

As used herein, the term "isotopomer" refers to isomers having the same number of each atom but differing in the isotope of at least one of the atoms.

An analyte labeled with an isobaric tag of Formula I is represented by Formula Ia:

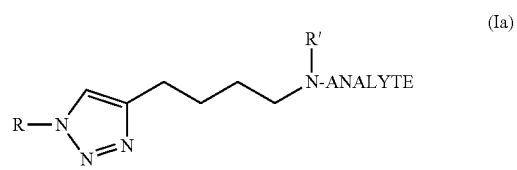

As mentioned, upon ionization and activation of the labeled analyte, an N3 nucleophilic attack of the 1,2,3-triazole ring occurs at the Cα of the protonated tertiary amine as shown in Scheme I:

Scheme I:

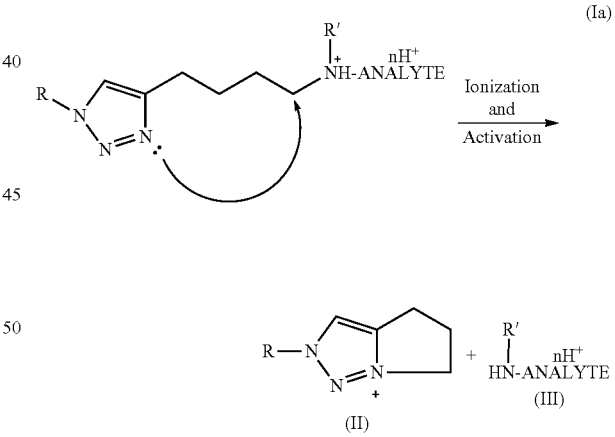

The structure of the compounds depicted in Formula I can be modified such that a carbon chain extends from the nitrogen of the tertiary amine linking the tertiary amine to the X reactive group. The (M) group below representing this carbon chain extension is selected such that the reagent remains soluble in its synthesis solvent and the solvent required for labeling of the analyte. Modification of the reagent at M should not affect the nucleophilic reaction, nor should it alter the effects of R or R'. Accordingly, in one embodiment, an isobaric reagent of the present invention is represented by Formula IV as shown:

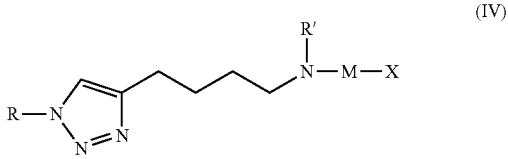

(IV)

wherein M is a hydrocarbon group (up to 10 carbons in length) or a hydrocarbon group containing oxygen (O) The hydrocarbon may also include nitrogen (N) so long as the desired activity is retained. In general, M can be (CH2)n-CO; (CH2)-CO—NH—(CH2)n-CO, or (CX)—CO, wherein n is 1, 2, 3, etc, so long as the carbon chain length does not exceed 10, and X is hydrogen, oxygen, or a methyl group.

In another embodiment, an isobaric reagent of the present invention has the general structure of Formula V, wherein Formula V has one less carbon in the carbon chain between the 1,2,3-triazole and the Cα carbon of Formulas IV and I, as shown:

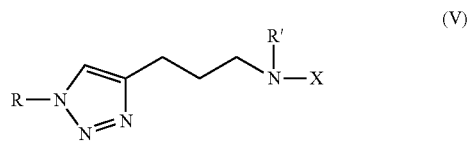

(V)

Upon ionization and activation, the reporter ion formed from formula V above will have the following structure II-V:

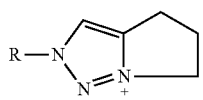

(II-V)

Isobaric reagents of the present invention are disclosed herein in more detail. For simplicity, embodiments are described with respect to Formula I, however, all embodiments encompass and can be applied to any one of Formulas I, IV, and V.

Reactive Group "X"

In one embodiment, the reactive group "X" of the isobaric reagent of Formulae I, IV or V is either an electrophile or a nucleophile that is capable of reacting with one or more reactive analytes of a sample. The reactive group "X" can be selected based on the analyte(s) that will be labeled with the reagent. Description of various analytes and cognate reactive groups are described in Pappin et al. (U.S. Patent Application Publication No. 2005/0148087) from which paragraphs 0062 through 0070 are incorporated by reference in their entirety.

The reactive group can be preexisting or it can be prepared in-situ. In-situ preparation of the reactive group can proceed in the absence of the reactive analyte or it can proceed in the presence of the reactive analyte. For example, a carboxylic acid group can be modified in-situ with a water-soluble carbodiimide, e.g. 1-(3-dimethylaminopropyl)-3-ethylcarbodiimide hydrochloride; EDC) to thereby prepare an electrophilic group that can be reacted with a nucleophile such as an alkyl or aryl amine group. In some embodiments, activation of the carboxylic acid group of a labeling reagent with EDC is performed in the presence of an amine (nucleophile) containing analyte. In some embodiments, the amine (nucleophile) containing analyte can also be added after the initial reaction with EDC is performed. In other embodiments, the reactive group can be generated in-situ by the in-situ removal of a protecting group. Accordingly, any existing or newly created reagent or reagents that can effect the derivatization of analytes by the reaction of nucleophiles and/or electrophiles are contemplated by the methods and compositions of this invention.

Where the reactive group X of the Formula-I based isobaric tag is an electrophile, it can react with a suitable nucleophilic group of the analyte or analytes. Where the reactive group X of the Formula-I based isobaric tag is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes to effect their derivatization such as proteins, peptides, nucleic acids, carbohydrates, lipids, steroids or other small molecules of less than 1500 daltons), are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group X of the Formula-I based isobaric tag can be an amine reactive group. For example, the amine reactive group can be an active ester. Active esters are well known in peptide synthesis and refer to certain esters that are easily reacted with the N-.alpha.-amine of an amino acid under conditions commonly used in peptide synthesis. The amine reactive active ester can be an N-hydroxysuccinimidyl ester (NHS), a N-hydroxysulfosuccinimidyl ester, a pentafluorophenyl ester (Pfp), a 2-nitrophenyl ester, a 4-nitrophenyl ester, a 2,4-dinitrophenylester, a 2,4-dihalophenyl ester, or an aryl-aldehyde boronic pinacol ester. It should be apparent that the active ester (e.g. N-hydroxysuccinimidyl ester) of any suitable labelling/tagging reagent described herein can be prepared using well-known procedures (See: Greg T. Hermanson (2008), "Bioconjugate Reagents," Bioconjugate Techniques, Part II, pages 213-742, Academic Press, (New York); also see: Innovation And Perspectives In Solid Phase Synthesis, Editor: Roger Epton, SPCC (UK) Ltd, Birmingham, 1990); both of which are herein incorporate by reference in their entirety.

The reactive group X of an isobaric tag of Formula I can be a mixed anhydride. Mixed anhydrides are known to efficiently react with amine groups to produce amide bonds.

The reactive group X of the Formula-I based isobaric tag can be a thiol reactive group. For example, the thiol reactive group can be a malemide, an alkyl halide, an aryl halide of an α-halo-acyl, an α-halo thione, or an α-halo imine. Halide or halo refers to the atoms fluorine, chlorine, bromine or iodine.

The reactive group X of the Formula-I based isobaric tag can be a hydroxyl reactive group. For example, the hydroxyl reactive group can be a trityl-halide or a silyl-halide reactive moiety. The trityl-halide reactive moieties can be substituted or unsubstituted.

Reporter Ion Side Group, R and Isotopomer R' Groups.

In one embodiment of the present invention, the reporter ion side group, R, and its isotopomer, R', each comprise at least (n) number of atoms that can be substituted, thereby providing a set of isobaric reagents having at least (n+1) number of distinct reporter ions.

FIG. 1 shows a general schematic for a set of isobaric reagents according to the present invention. In one embodiment of the present invention, a method of designing a set of isobaric tags for labeling (m) number of samples comprises selecting an R group having at least (m−1) number of atoms that can be isotopically substituted.

In one embodiment, a kit includes (m) number of reagents, wherein (m) number of reagents includes a first reagent (having $R_1$, $R_1'$), at least a second reagent (having $R_2$, $R_2'$) up to (m) number of reagents (having $R_m$, $R_m'$). For all reagents in the kit, the sum of R+R' for each reagent is constant. The first reagent can represented by Formula VI as shown.

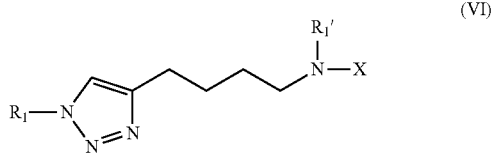

(VI)

The at least a second reagent is represented by Formula VII:

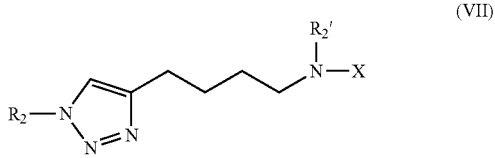

(VII)

Subsequent reagents can be represented by Formula VIII

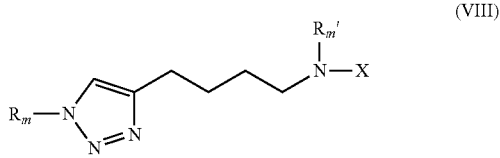

(VIII)

For Formulas VI, VII and VIII above,

R is a hydrocarbon group or a hydrocarbon group containing one or more heteroatoms of nitrogen and/or oxygen;

R' is an isotopomer of R; and

X is a reactive group capable of coupling to an analyte;

wherein the sum of (the mass of R+the mass of R') for each reagent is constant; and wherein the mass of each R of each reagent differs from the mass of every other R, and the mass of each R' of each reagent differs from the mass of every other R' for the set of reagents in the kit.

In one embodiment of the present invention, R is any hydrocarbon moiety that can be synthesized into an isobaric reagent of Formulas I, IV or V. In another embodiment, the hydrocarbon moiety includes one or more heteroatoms, such as nitrogen, one or more oxygen, and sulfur. Non-limiting examples of R groups include unsaturated and saturated hydrocarbon groups—alkyl, alkenyl, alkynyl—such as methyl, ethyl, propyl, isopropyl, butyl, isobutyl, allyl, as well as cyclic hydrocarbons (e.g. cyclohexyl, cyclohexenyl); aromatic groups, such as aryl, arylalkyl, aralkyl, alkaryl (e.g. phenyl, benzyl, etc.); hetero-substituted hydrocarbon and cyclohydrocarbon groups; polyethylene glycol; other ethers, etc.

The size of the reporter group is ideally as small as possible while providing enough atoms for the desired set of distinct reporter ions. Additionally, the reporter ion group R is selected such that it is soluble during its synthesis and does not precipitate, and will maintain solubility in the analyte labeling solvent.

As the R and R' groups allow the mass balance of the reagent(s) to be tuned, and do not participate in any reaction, the skilled person will recognize that an R group according to the present invention is selected such that it does not interfere with the nucleophilic reaction of the 1,2,3-triazole with the Cα carbon of the tertiary amine.

As will also be apparent to the skilled person, for practical purposes, the R group only needs to have as many atoms (n) as necessary to provide for (n+1) distinct reporter ions. In some embodiments, the atoms of the R group are selected such that the isotope substitutions are the most cost effective and/or easiest to synthesize. Isotopic substitutions for (H) hydrogen, (C) carbon, (N) nitrogen, and (O) oxygen are well known in the art. For example, isotopes of carbon ($^{12}C$, $^{13}C$, and $^{14}C$), nitrogen ($^{14}N$ and $^{15}N$), oxygen ($^{16}O$, $^{17}O$, and $^{18}O$) and hydrogen (hydrogen, deuterium (D) and tritium (T)) exist and can be used in the preparation of a diverse group of reporter moieties. Examples of stable heavy atom isotopes include $^{13}C$, $^{15}N$, $^{18}O$, and deuterium (D or $^2H$). These examples, however, are not exclusive, as other light and heavy atom isotopes can also be used in the reporter. Resources for design and synthesis of compounds for the R and R' group comprising light and heavy atom isotopes are available from various commercial sources, such as Cambridge Isotope Laboratories, Andover, Mass., and Isotec (a division of Sigma-Aldrich).

The R group on the 5,6-membered ring reporter ion (Formula II) is selected such that the resulting R-reporter ion has a unique mass (or mass to charge ratio, m/z) that is not coincident with other possible fragments (e.g. peptide fragments including b and y ions) during mass analysis.

For example, for protein mass analysis using collisional activation, mass zones which are known to be available for this type of mass analysis include the following: 10-14 m/z; 19-22 m/z; 24-26 m/z; 31-38 m/z; 40-40 m/z; 46-50 m/z; 52-52 m/z; 58-58 m/z; 61-69 m/z; 71-71 m/z; 74-83 m/z; 89-97 m/z; 103-109 m/z; 113-119 m/z; 121-125 m/z; 128-128 m/z; 131-135 m/z; 137-147 m/z; 149-154 m/z; 156-156 m/z; 160-174 m/z; 177-182 m/z; 184-184 m/z; 188-189 m/z; 191-191 m/z; 202-207 m/z; 210-210 m/z; 216-222 m/z; and 224-226 m/z.

Figure 2:
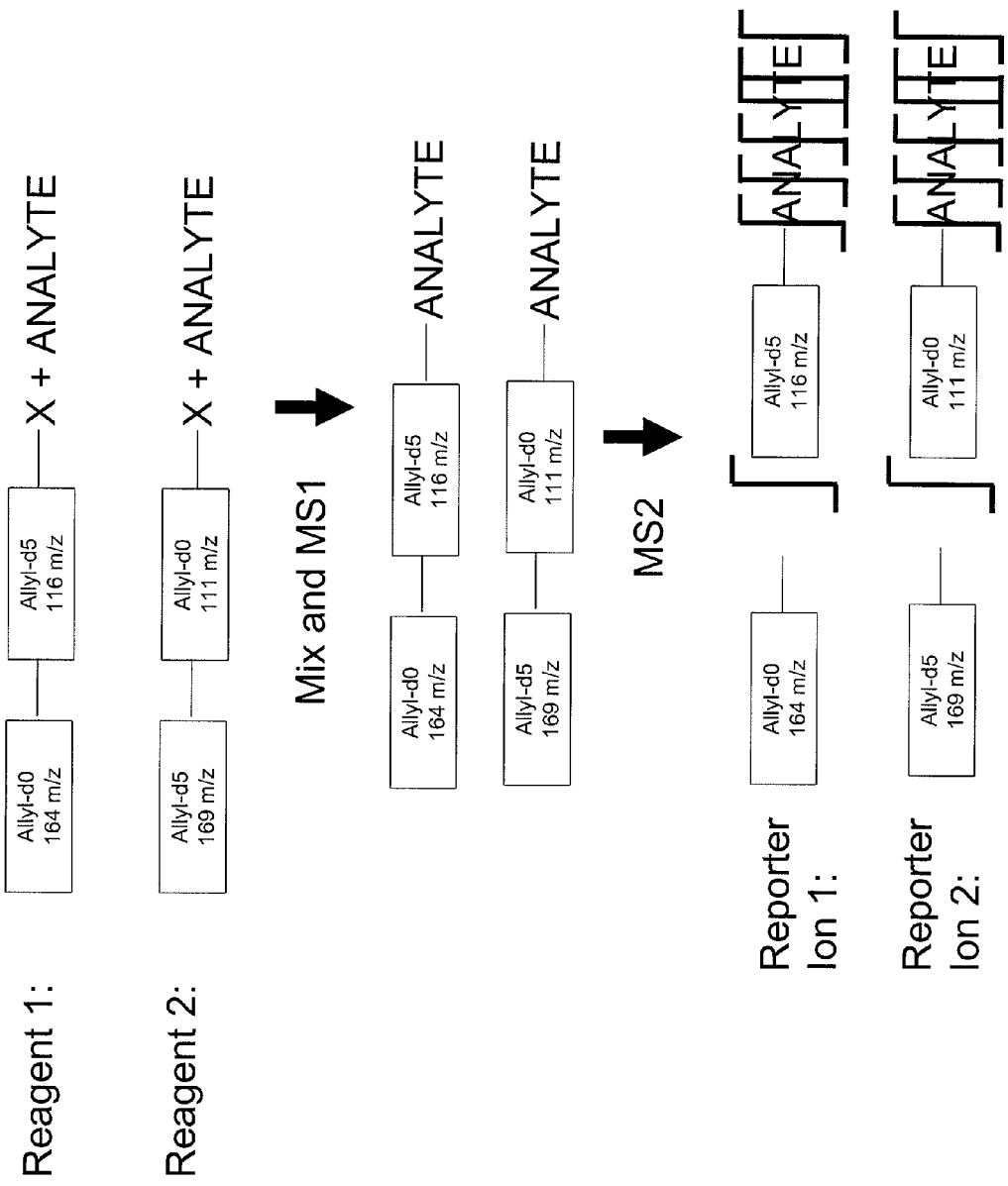
FIG. 2 is a schematic of example isobaric reagents according to an embodiment of the present invention.

By way of example, in one embodiment of the present invention, an isobaric reagent having the generic structure of Formula IV is provided, wherein R is an allyl group and M is $CH_2$—CO. Specific examples of two isobaric reagents are schematically depicted in FIG. 2 and shown below, wherein R is an allyl group. Using allyl-$D_0$ (allyl) and allyl-$D_5$ (deuterated allyl), two isobaric tags are formed that result in two distinct reporter ions—the allyl-$D_0$-(Reporter Ion 1, FIG. 2) having a mass/charge ratio of 164 m/z and the allyl-$D_5$ (Reporter Ion 2, FIG. 2) having a mass/charge ratio of 169 m/z. Formula VIII depicts an isobaric reagent when R is allyl-$D_0$ and R' is allyl-$D_5$ and Formula IX depicts an isobaric reagent when R is allyl-$D_5$ and R' is allyl-$D_0$.

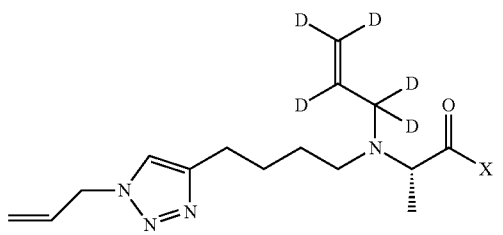

(VIII)

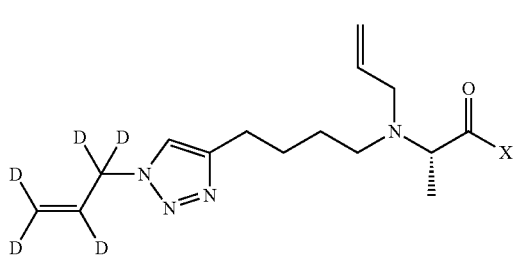

(IX)

TABLE 1

| Reagent | R group | R' group |
|---|---|---|
| 1 | allyl-$D_0$ | allyl-$D_5$ |
| 2 | allyl-$^{13}C$ | allyl-$(^{13}C)_3$-$D_1$ or allyl-$D_4(^{13}C)$ |
| 3 | allyl-$(^{13}C)_2$ | allyl-$(^{13}C)_3$ |
| 4 | allyl-$(^{13}C)_3$ | allyl-$(^{13}C)_2$ |
| 5 | allyl-$(^{13}C)_3$-$D_1$ or allyl-$D_4(^{13}C)$ | allyl-$(^{13}C)$ |
| 6 | allyl-$D_5$ | allyl-$D_0$ |

In one embodiment of the invention, a set of isobaric reagents is represented by Formula I, wherein R is an ethylene glycol group, represented by HO—[CH2-CH2-O—]$_n$—CH2-CH2-(LG/N3), shown here as a precursor attached to a leaving group (LG) or an azide (N3). An isobaric reagent having these R and R' groups can be synthesized by following the synthesis scheme of FIG. 5 using OTs (O-tosylate) as the leaving group, such that precursor R and R' are ethylene glycol-(N3) and ethylene glycol-(OTs), respectively. For an exemplary set of 9 isobaric reagents (when n=1 in the above ethylene glycol formula), the R and R' groups are as follows, with the precursor OTs and N3 groups also shown in Table 2 below.

TABLE 2

| Reagent | R group-(shown as precursor) | R' group (shown as precursor) |
|---|---|---|
| 1 | HO—CH2—CH2—O—CH2—CH2—(N3) | HO—CD2—CD2—O—CD2—CD2—(OTs) |
| 2 | HO—$^{13}$CH2—CH2—O—CH2—CH2—(N3) | HO—CD2—CD2—O—$^{13}$CD2—CH2—(OTs) |
| 3 | HO—CD2—CH2—O—CH2—CH2—(N3) | HO—CD2—CD2—O—CD2—CH2—(OTs) |
| 4 | HO—$^{13}$CD2—CH2—O—CH2—CH2—(N3) | HO—CD2—CD2—O—$^{13}$CH2—CH2—(OTs) |
| 5 | HO—CD2—CD2—O—CH2—CH2—(N3) | HO—CD2—CD2—O—CH2—CH2—(OTs) |
| 6 | HO—CD2—CD2—O—$^{13}$CH2—CH2—(N3) | HO—$^{13}$CD2—CH2—O—CH2—CH2—(OTs) |
| 7 | HO—CD2—CD2—O—CD2—CH2—(N3) | HO—CD2—CH2—O—CH2—CH2—(OTs) |
| 8 | HO—CD2—CD2—O—$^{13}$CD2—CH2—(N3) | HO—$^{13}$CH2—CH2—O—CH2—CH2—(OTs) |
| 9 | HO—CD2—CD2—O—CD2—CD2—(N3) | HO—CH2—CH2—O—CH2—CH2—(OTs) |

The corresponding reporter ions (Reporter Ion 1 and Reporter Ion 2, FIG. 2) for reagents VIII and IX are shown below as VIII-R and IX-R, having masses of 164 m/z and 169 m/z, respectively.

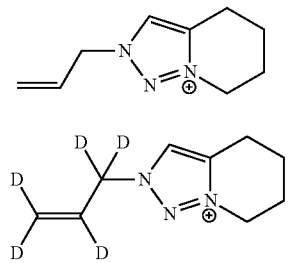

(VIII-R)

(IX-R)

Figure 3:
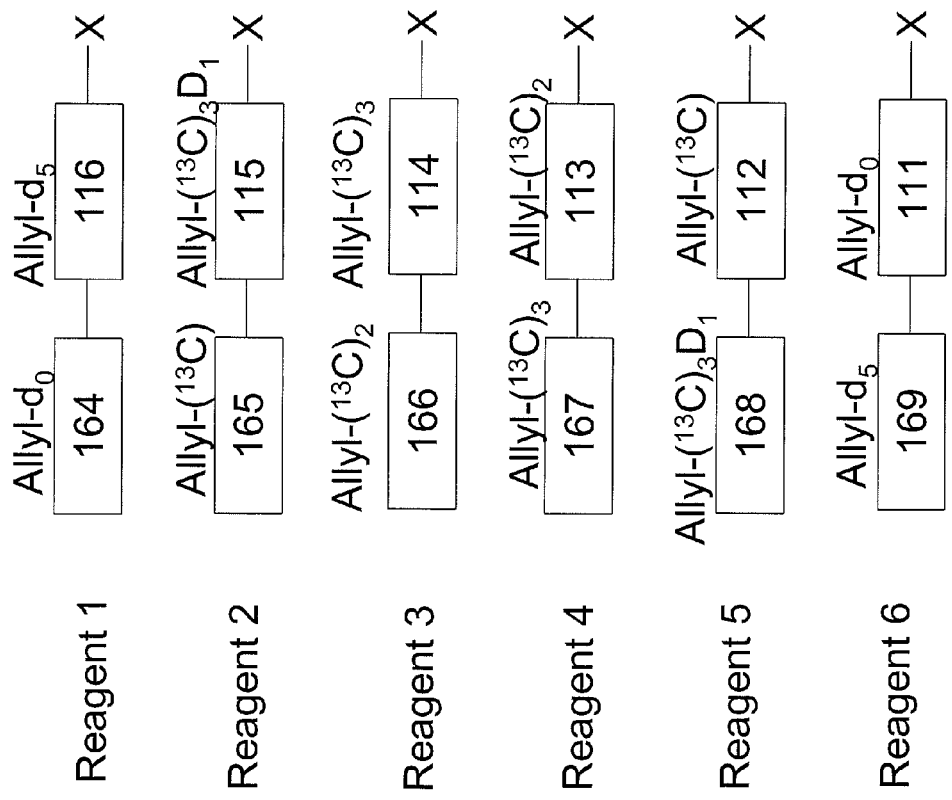
FIG. 3 is a schematic of a set of isobaric reagents according to an embodiment of the present invention.

The schematic in FIG. 3 shows an exemplary set of 6 isobaric reagents according to one embodiment of the present invention. As shown, R is an allyl group, and can be synthesized as further described herein using allyl-Br (or any leaving group) and allyl-azide, and M is CH2-CO (based on Formula IV). Reagent 1 and Reagent 6 are the same as VIII and IX shown above. Reagents 2-5 are substituted with $^{13}$C as shown, such that the R and R' groups are as shown in Table 1 below.

In another example, the R and R' ethylene glycol structure of HO—[CH2-CH2-O—]n -CH2-CH2-(LG/N3) can be used wherein n=2, 3, 4, 5, etc. The numbers of these repeated ethylene glycol groups can increase so long as the solubility of the reagent is maintained in the synthesis reaction solvent, as well as in the analyte labeling solvent.

It is noted that the mass of some reporter ions in a set may overlap with background and fragments from the analyte, and, therefore cannot be used. In the ethylene glycol sample above, more than 9 reagents can be designed when n is greater than 1. However, not all resulting reporter ions will fall within the available zones as discussed above. These mass calculations in view of the list of available mass zones for a particular type of analysis can be predicted and calculated by one skilled in the art so that reagents are not synthesized that will not be useful. The mass zones that are available will vary depending on the type of mass analysis.

Figure 5:
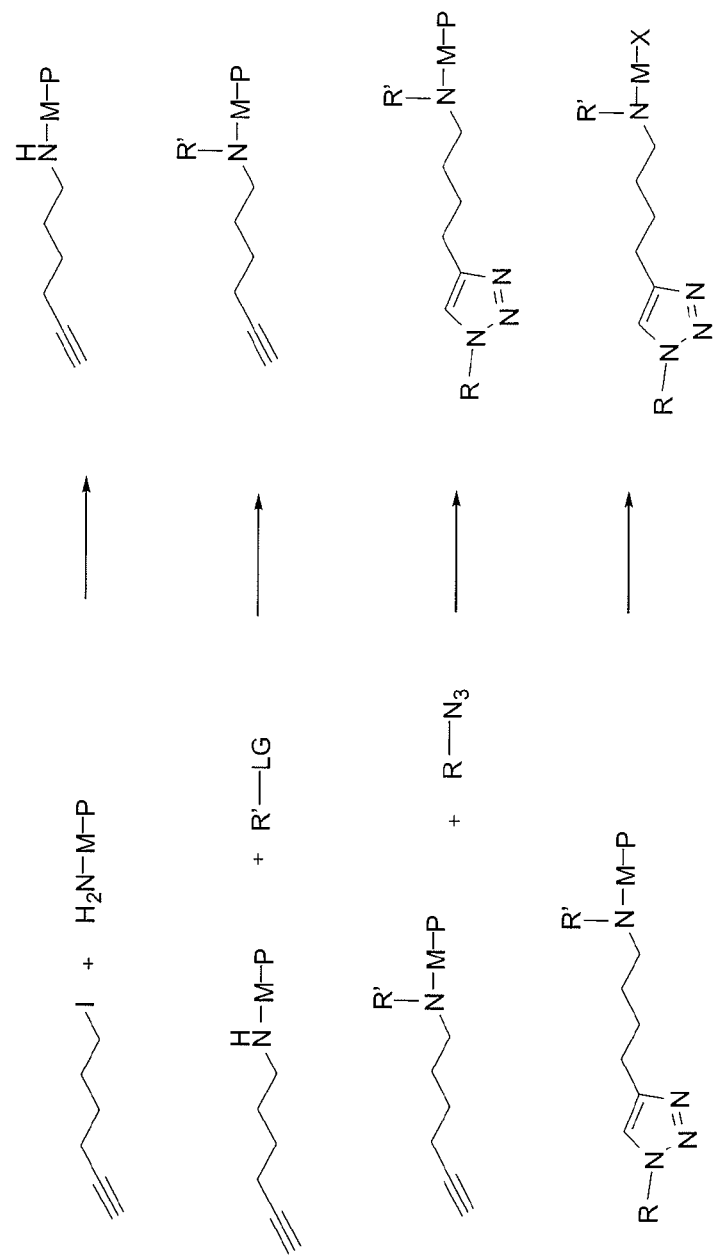
FIG. 5 is a schematic showing synthesis of isobaric reagents according to an embodiment of the present invention.

In one embodiment of the invention, a set of isobaric reagents is represented by Formula I, wherein R is a benzene group. With reference to FIG. 5, R—$N_3$ and R'-LG can be all the possible isotopomers of $C_6H_5$—$CH_2$. For example $C_6H_5$—$CH_2$—$N_3$ or $C_6H_5$—$CH_2$-LG can be used, and then each atom can be isotopically substituted independently up to $^{13}C_6D_5$-$^{13}CD_2$ to give a set of at least 15 isobaric reagents.

Reporter Region and Mass Balancing Region

In addition to isotopic substitutions in R and R', substitutions can also be made within the Reporter Region and the Mass Balancing Region. The Reporter Region includes the R group, the 1,2,3-triazole ring, and the hydrocarbon chain extending from the 1,2,3-triazole ring. The Mass Balancing Region includes the R' group, the tertiary amine, and the M group linking the tertiary amine to the reactive group. These additional positions provide more options for designing a set of isobaric reagents having the easiest and most cost-effective synthesis.

Formula V is modified to give Formula X to show the Reporter Region and the Mass Balancing Region.

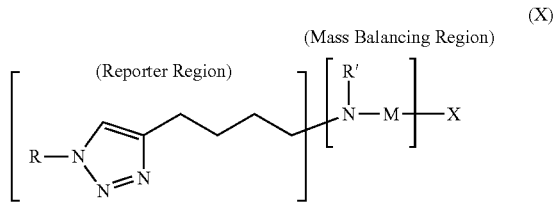

(X)

In one embodiment, a set of isobaric reagents comprises at least two reagents, wherein the first reagent and at least a second reagent are both represented by Formula X:

wherein

R is a hydrocarbon group or a hydrocarbon group containing one or more heteroatoms;

R' is an isotopomer of R;

M is a linker group as described herein;

X is a reactive group capable of reacting with an analyte;

and wherein the sum of the masses of (Reporter Region+ Mass Balancing Region) for each reagent is constant, and the mass of each Reporter Region is different from every other Reporter Region mass, and the mass of each Mass Balancing Region is different from every other Mass Balancing Region for each reagent in the set of isobaric reagents.

Figure 4:
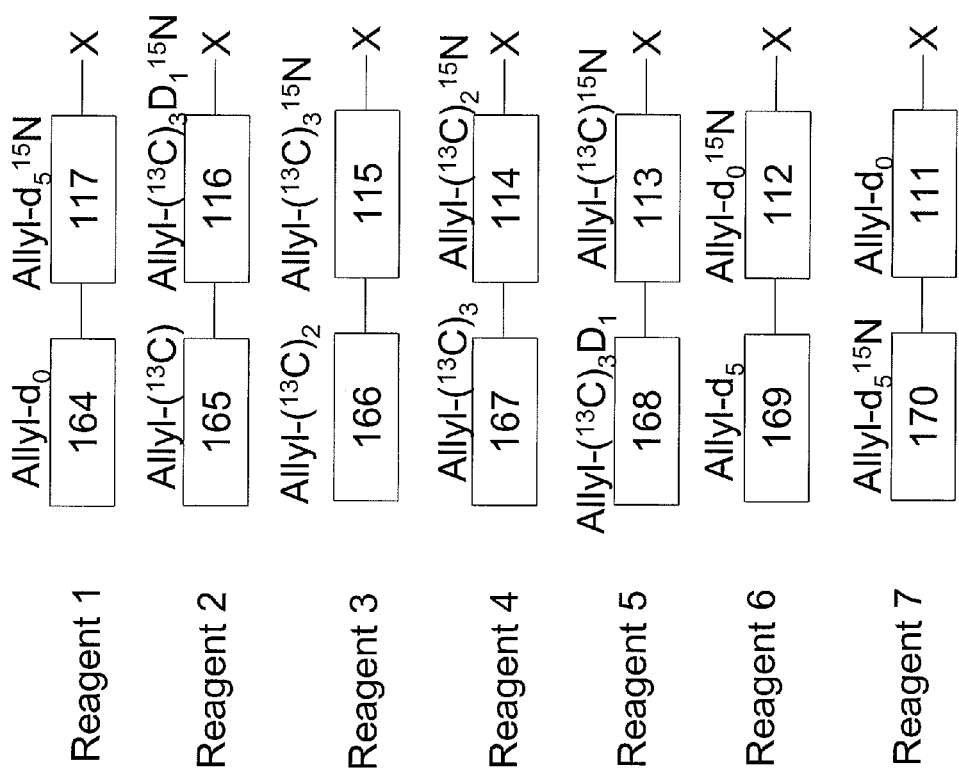
FIG. 4 is a schematic of a set of isobaric reagents according to an embodiment of the present invention.

Isotopic substitutions in the Reporter Region and Mass Balancing Region can occur in various combinations. For example, as shown below and in FIG. 4, by adding a $^{15}$N to the tertiary amine in the Mass Balancing Region of Formula X, it is possible to generate at least 7 distinct reporter ions when R is an allyl group and M is CH2-CO. An example Reagent 1 (Formula XI) is shown below showing the $^{15}$N at the tertiary amine. In the example, all of the reporter ions of Reagents 1-6 of FIG. 4 are the same as those of FIG. 3, and the reporter ion of Reagent 7 has a $^{15}$N in the 1,2,3-triazole ring, resulting in a mass of 170 m/z. Example Reagent 7 is shown in Formula XII.

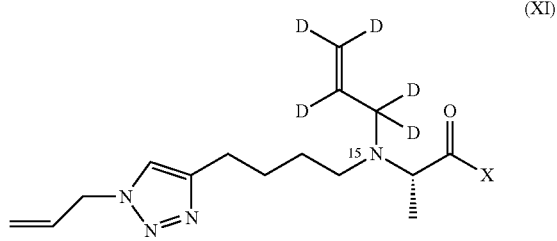

(XI)

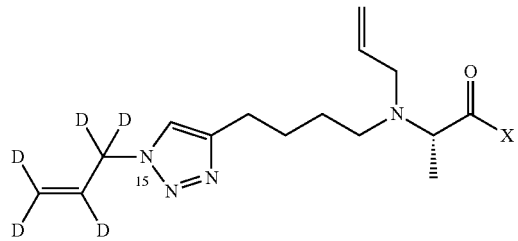

(XII)

As will be apparent to one skilled in the art, the type of isotopic substitutions made in the Reporter Region does not have to be the same type of substitution in the Mass Balancing Region, as any isotopic substitution that results in a balance of the masses can be utilized, so long as in a set of isobaric reagents, the sum of the masses of (Reporter Region)+(Mass Balancing Region) is constant for the set of reagents.

It will also be apparent to one skilled in the art, that, with respect to Formula X, there are 18 possible atomic positions in the Reporter Region that can be isotopically substituted, and in order to take advantage of these positions, M is selected/designed to provide enough atoms to the Mass Balancing Region.

Synthesis of Isobaric Tags

Synthesis of an isobaric reagent according to the present invention is shown schematically in FIG. 5, wherein R, R', and X are as defined for Formulas I, IV, and V, herein, P is a protecting group to protect the bonding site for the reactive group X, and LG represents any leaving group, including, but not limited to a halogen, O-toluenesulfonyl, triflate, tosylate, and mesylate. A leaving group is defined as any moiety that will stabilize an incipient negative charge in a reaction. An example of a suitable protecting group (P) is an ester group, or any functional group that would retain the desired activity. It will be apparent to the skilled person the type of protecting group (P) that is suitable for the selected M (if M is present) and X groups.

The synthesis of Formula I, IV or V having variable R and R' groups is straightforward as R' can be incorporated using R'-LG, and R can be added using R-azide (N3). Methods for synthesizing a Formula-I based isobaric reagent are well known in the art, and will vary depending on the selection of R, R', and X in Formula I. The skilled person having selected R, R', and X moieties can synthesize the desired set of isobaric tags with reference to FIG. 5, and the examples provided herein. (See for example, Hermanson, 2008, *Bioconjugate Techniques*, 2nd Edition, Academic Press, Inc.) An exemplary method of an isobaric tag when R is a deuterated allyl group (allyl-$D_5$), R' is allyl-$D_0$, and X is N-hydroxysuccinimide ester (NHS) is provided in detail in Example 1 and shown schematically in FIG. 6.

Other non-allylic R-group-containing reagents having various X reactive groups can be synthesized using suitable reaction conditions and organic synthesis techniques, as known in the art.

Labeling of Analytes

Analytes are labeled with an isobaric tag of the present invention according to well established methods. (See for example, US Patent Application Publication No. 2005/0148087, paragraphs 0107 through 0110 are herein incorporated by reference; and Hermanson, 2008, Ibid). The labeling occurs by reacting a functional group of the analyte with the reactive group (X) of an isobaric tag of Formula I. As discussed previously, the functional group on the analyte can be one of an electrophile or a nucleophile and the reactive group X of the isobaric tag can be the other of the electrophile or a nucleophile. The electrophile and nucleophile can react to form a covalent link between the analyte and the labeling reagent.

As also known in the art, the labeling reaction can take place in solution. In some embodiments, one of the analyte or the labeling reagent can be support bound. The labeling reaction can be performed in aqueous conditions. Aqueous conditions can be selected for the labeling of biomolecules such as proteins, peptides, and nucleic acids. The labeling reaction can be performed in organic solvent or a mixture of organic solvents. Organic solvents can be selected for analytes that are small molecules. Mixtures of water and organic solvent or organic solvents can be used across a broad range. For example, a solution of water and from about 60 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), and methanol, ethanol, propanol, butanol, and other alcohols.

When performing a labeling reaction, the pH can be modulated, to within the range of 4-10. The pH can alternatively be outside this range. Generally, the basicity of non-aqueous reactions can be modulated by the addition of non-nucleophilic organic bases. Non-limiting examples of suitable bases include N-methylmorpholine, triethylamine, and N,N-diisopropylethylamine. Alternatively, the pH of water-containing solvents can be modulated using biological buffers such as (N-[2-hydroxyethyl]piperazine-N'-[2-ethanesulfonic acid) (HEPES) or 4-morpholineethane-sulfonic acid (MES), or inorganic buffers such as sodium carbonate and/or sodium bicarbonate. Because at least one of the reactive groups can be electrophilic, it can be desirable to select the buffer to not contain any nucleophilic groups. Those of skill in the art will appreciate other buffers that can be used to modulate the pH of a labeling reaction, with the application of ordinary experimentation, so as to facilitate the labeling of an analyte with a labeling reagent.

Labeling of peptides using isobaric tags of Formula VIII and IX is disclosed in detail in Example 2.

Methods for Detecting, Identifying and/or Quantifying Analytes

There are many known methods in the art for mass analysis of isobaric labeled analytes, and many possible methods after the analyte is labeled. Typically, the labeling reaction is quenched using a de-salting method (reference here). If the reactants from this procedure are removed during MS analysis, then a purification step is optional. However, for proteomic analysis, wherein one or more peptide or protein samples are to be quantified, a purification step can be implemented to further purify the labeled peptides/proteins. For example, labeled peptides/proteins may be affinity purified if the peptides/proteins were synthesized or expressed with a corresponding affinity tag, for example, biotin, 6-HIS, etc., such that they can be purified by the corresponding affinity column. Standard procedures for separation even in the absence of an affinity tag can be implemented, including high pressure liquid chromatography (HPLC). In one embodiment, analytes labeled with isobaric tags of the present invention are chromatographically separated using multi-dimensional HPLC and analyzed by MS and MS/MS techniques.

Mass Spectrometers/Mass Spectrometry (MS):

The methods of this invention can be practiced using tandem mass spectrometers and other mass spectrometers that have the ability to select and fragment molecular ions. Techniques of using mass spectrometry (MS) and tandem mass spectrometry (MS/MS) for detecting and quantifying labeled analytes, especially, labeled peptides and proteins, are well known in the art. Description of the use of MS and MS/MS for labeled analytes is described in Pappin et al. U.S. Patent Application Publication No. 2005/0148087, of which paragraphs 0089 through 0101 are herein incorporated by reference in their entirety.

Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-induced dissociation (CID), pulse Q dissociation (PQD), high energy C-trap dissociation (HCD), as well as CID-HCD hybrid methods). For a description of these methods, see Kucher et al. 2009, *J. of Proteome Research*, 8:4743-4752; and Bantscheff et al., 2008, *Molec. and Cell. Proteomics* 7.9, 1702-1713.) For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. FAB (Fast atom bombardment) is an ionization technique also used in mass spectrometry, wherein the material to be analyzed is mixed with a non-volatile chemical protection environment called a matrix and is bombarded under vacuum with a high energy (4000 to 10,000 electron volts) beam of atoms. (See for example, Morris H R, et al. (1981). "Fast atom bombardment: a new mass spectrometric method for peptide sequence analysis". *Biochem. Biophys. Res. Commun.* 101 (2): 623-31).)

Additional mass spectrometry instruments and fragmentation methods include post-source decay in MALDI-MS instruments and high-energy CID using MALDI-TOF (time of flight)-TOF MS. For a review of tandem mass spectrometers please see: R. Aebersold and D. Goodlett, Mass Spectrometry in Proteomics. Chem. Rev. 101: 269-295 (2001). Also see U.S. Pat. No. 6,319,476, herein incorporated by reference, for a discussion of TOF-TOF mass analysis techniques.

Fragmentation by Dissociative Energy Levels t is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID). Those of ordinary skill in the art of mass spectrometry will appreciate that other exemplary techniques for imposing dissociative energy levels that cause fragmentation include, but are not limited to, photo dissociation, electron capture and surface induced dissociation.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter/linker moiety depends upon the nature of the analyte or the reporter/linker moiety. Accordingly, the dissociative energy levels can be adjusted so that the analytes and/or the labels (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission. Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as serine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., Rapid Commun. Mass Spectrom., 12: 837-842) (1998). Accordingly, the peptide bond of a Z-pro dimer or Z-asp dimer, wherein Z is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. J. Am. Soc. Mass Spectrom., 5: 976-989 (1994)) and MASCOT (Perkins, D. et al. Electrophoresis, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, Genetics, 16: 5-8 (2000) and Yates, J. R., Electrophoresis 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids.

EXAMPLE 1

Figure 6:
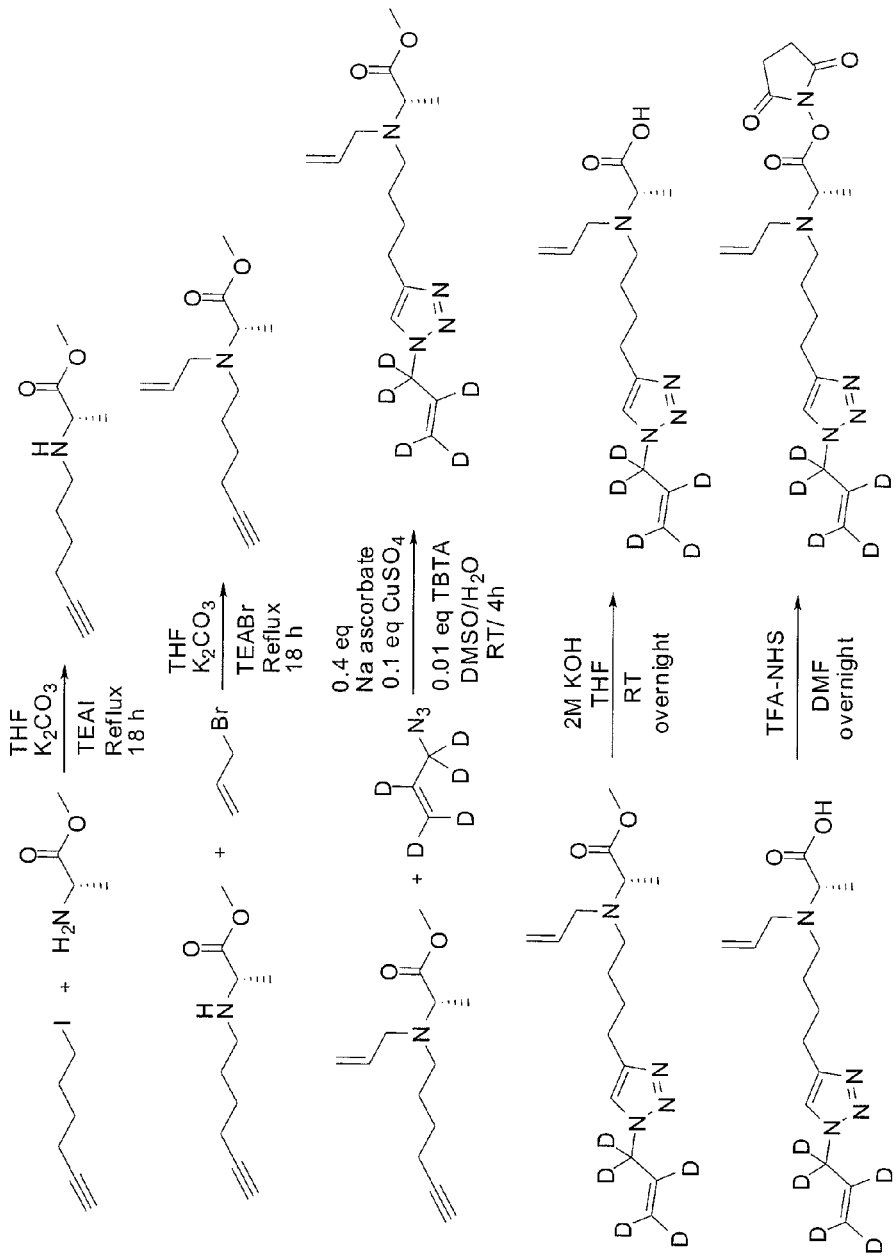
FIG. 6 is a schematic showing an example synthesis of isobaric reagents according to an embodiment of the present invention.

Synthesis of Isobaric Reagent Tags VIII and IX
(FIG. 6)

N-(5-hexynyl) L-alanine methyl ester

In a flame-baked, two neck 100 mL round bottom flask, 20 mmol of L-alanine methyl ester hydrochloride (2.8 g), 40 mmol of $K_2CO_3$ (5.53 g), and 20 mmol of tetrabutylammonium iodide (TBAI, 7.39 g) were charged under a stream of dry $N_2$ gas. 35 mL of tetrahydrofuran (THF) was slowly added and the mixture was stirred for 15 min at room temperature. 2.6 mL of 6-iodo-hex-1-yne was added dropwise while the mixture was stirred. The reaction mixture was refluxed at ~70° C. for 15-18 h with TLC check. After consumption of the starting material, the mixture was cooled to room temperature, diluted by diethylether, and filtered. The filtrate was further diluted by diethylether and filtered again. The solvent was removed by rotavap and the crude product was purified by flash chromatography on silica gel (1:2=Hexane/EtOAc, 1% triethylamine) to give N-(5-hexynyl) L-alanine methyl ester (2.044 g, 11.2 mmol) as a yellow oil. Yield: 56%. $R_f$=0.27 (1:1=Hexane/EtOAc); ESI-MS [M+H]$^+$= 184.1 m/z; $^1$H NMR (300 MHz, CDCl$_3$): δ 3.70 (s, 3H), 3.32 (q, J=7.0 Hz, 1H), 2.53 (m, 2H), 2.18 (m, 2H), 1.92 (t, J=2.6 Hz, 1H), 1.56 (m, 5H), 1.27 (d, J=7.0 Hz, 3H); $^{13}$C NMR (75 MHz, CDCl$_3$): δ 176.29, 84.21, 68.41, 56.61, 51.74, 47.41, 29.20, 26.01, 19.11, 18.23.

N,N-(5-hexynyl)(allyl-D$_0$) L-alanine methyl ester and N,N-(5-hexynyl)(allyl-d$_5$) L-alanine methyl ester In a flame-baked, two neck 50 mL round bottom flask, 10 mL THF was charged under the stream of dry N$_2$ gas. 6 mmol of K$_2$CO$_3$ (0.83 g), and 6 mmol of tetrabutylammonium bromide (TBAB, 1.93 g) were slowly added and stirred for 15 min in room temperature. 3 mmol of N-(5-hexynyl) L-alanine methyl ester (0.55 g), and 4.5 mmol of allyl bromide-D$_0$ (0.544 g, 0.38 mL) was slowly added dropwise using the syringe while the mixture is stirred. The reaction mixture was heated at ~55° C. and reacted for 8 h with TLC check. After consumption of the starting material, the mixture was cooled to room temperature, diluted by diethylether, filtered, and repeated filtered twice to remove the remaining TBAB completely. The solvent was removed by rotavap and the crude product was purified by flash chromatography on silica gel (20:1=Hexane/EtOAc) to give N,N-(5-hexynyl)(allyl-D$_0$) L-alanine methyl ester (0.378 g, 1.69 mmol) as a transparent oil. Yield: 56%. $R_f$=0.4 (5:1=Hexane/EtOAc); ESI-MS [M+H]$^+$=224.2 m/z; $^1$H NMR (300 MHz, CDCl$_3$): δ 5.79 (m, 1H), 5.12 (m, 2H), 3.67 (s, 3H), 3.54 (q, J=7.3 Hz, 1H), 3.18 (m, 2H), 2.53 (m, 2H), 2.18 (m, 2H), 1.93 (t, J=2.7 Hz, 1H), 1.52 (m, 4H), 1.24 (d, J=7.3 Hz, 3H); $^{13}$C NMR (75 MHz, CDCl$_3$): δ 174.45, 136.86, 116.78, 84.47, 68.24, 57.79, 54.20, 51.21, 49.85, 27.40, 26.07, 18.26, 14.88.

0.457 g of N,N-(5-hexynyl)(allyl-d$_5$) L-alanine methyl ester (2.0 mmol) was obtained by the same procedure described above by using 3.55 mmol of allyl bromide-d$_5$ (0.448 g). Yield: 67%. $R_f$=0.4 (5:1=Hexane/EtOAc); ESI-MS [M+H]$^+$=229.3 m/z; $^1$H NMR (500 MHz, CDCl$_3$): δ 3.68 (s, 3H), 3.54 (q, J=7.08 Hz, 1H), 2.53 (m, 2H), 2.18 (m, 2H), 1.93 (t, J=2.68 Hz, 1H), 1.52 (m, 4H), 1.25 (d, J=7.08 Hz, 3H); $^{13}$C NMR (125 MHz, CDCl$_3$): δ 174.47, 136.16 (t, J=23.48 Hz), 116.25 (quintet, J=23.47 Hz), 84.47, 68.27, 57.76, 53.28 (quintet, J=18.41 Hz), 51.22, 49.79, 27.39, 26.07, 18.26, 14.90.

Allyl-D0 Azide and Allyl-D5 Azide 0.5 M NaN$_3$ in DMSO was prepared as described in the literature by stirring the mixture at room temperature overnight (Alvarez, S. G. & Alvarez, M. T. Synlett, 413-414 (1997). 1.1 eq of 0.5 M NaN$_3$ solution was mixed with the appropriate amount of allyl bromide (D0/D5) and stirred overnight. TLC was monitored for the complete consumption of the starting material and unwanted dimerization of allyl azides was not observed in this condition. The resulting mixtures were used for the next steps without further purification or analysis.

N,N-(4-(1-allyl-d$_5$-1H-1,2,3-triazol-4-yl)butyl)(allyl-D$_0$) L-alanine methyl ester and N,N-(4-(1-allyl-D$_0$-1H-1,2,3-triazol-4-yl)butyl)(allyl-D$_5$) L-alanine methyl ester The literature procedure was followed with some modifications (Kacprzak, K., Synlett, 943-946 (2005)). For in-situ preparation of allyl-d$_5$ azide solution (~1.2 eq), 1.7 mmol of N,N-(5-hexynyl)(allyl-D$_0$) L-alanine methyl ester (0.378 g), 0.17 mmol of CuSO$_4$.5H$_2$O (42.5 mg, 0.1 eq), 0.68 mmol of sodium ascorbate (134.7 mg, 0.4 eq), 0.017 mmol of tris[(1-t-butyl-1H-1,2,3-triazol-4-yl)methyl]amine (TBTA) (7.3 mg, 0.01 eq), and additional 2 mL of DMSO were added and stirred for 2 h at room temperature. 2.4 mL of water was then added and stirred for additional 2 h with monitoring TLC. After the complete consumption of the starting material, 4 mL of 1M NH$_4$OH was added to remove residual CuN$_3$ and (Cu)$_2$N$_3$. The mixture was diluted by additional water and ethyl acetate. The aqueous layer turned blue due to the coordination of ammonia to copper ions. The organic layer was separated, and further extracted by ethyl acetate three times. The combined organic layer was then washed by brine, dried over MgSO$_4$ and concentrated by rotavap. The crude product was purified by flash chromatography on silica gel (1:1=Hexane/EtOAc, 1% triethylamine) to give N,N-(4-(1-allyl-d$_5$-1H-1,2,3-triazol-4-yl)butyl)(allyl-D$_0$) L-alanine methyl ester (0.379 g, 1.22 mmol) as a transparent oil. Yield: 72%. $R_f$=0.3 (1:1=Hexane/EtOAc); ESI-MS [M+H]$^+$=312.3 m/z, CID of [M+H]$^+$ produced 169.1 m/z fragment; $^1$H NMR (500 MHz, CDCl$_3$): δ 7.25 (s, 1H), 5.76 (m, 1H), 5.14 (dd, J=17.1, 1.22 Hz, 1H), 5.04 (d, J=10 Hz, 1H), 3.64 (s, 3H), 3.51 (q, J=7.08 Hz, 1H), 3.21 (dd, J=14.6, 5.6 Hz, 1H), 3.09 (dd, J=14.4, 6.9 Hz, 1H), 2.68 (t, J=7.6 Hz, 2H), 2.52 (m, 2H), 1.54 (m, 4H), 1.21 (d, J=7.08 Hz, 3H); $^{13}$C NMR (125 MHz, CDCl$_3$): δ 174.46, 148.43, 136.81, 130.94 (t, J=24.9 Hz), 120.40, 119.21 (quintet, J=24.9 Hz), 116.82, 57.85, 54.25, 51.85 (quintet, J=23.9 Hz), 51.24, 50.20, 27.97, 27.06, 25.54, 14.83.

1.59 mmol of N,N-(5-hexynyl)(allyl-d$_5$) L-alanine methyl ester (0.363 g) was used for the same reaction described above to give N,N-(4-(1-allyl-D$_0$-1H-1,2,3-triazol-4-yl)butyl)(allyl-d$_5$) L-alanine methyl ester (0.341 g, 1.10 mmol) as a transparent oil. Yield: 69%. $R_f$=0.3 (1:1=Hexane/EtOAc); ESI-MS [M+H]$^+$=312.3 m/z, CID of [M+H]$^+$ produced 164.1 m/z fragment; $^1$H NMR (500 MHz, CDCl$_3$): δ 7.25 (s, 1H), 5.98 (m, 1H), 5.30 (dd, J=10, 0.9 Hz, 1H), 5.25 (d, J=17.1 Hz, 1H), 4.91 (d, J=6.1 Hz, 2H), 3.65 (s, 3H), 3.51 (q, J=7.1 Hz, 1H), 2.69 (t, J=7.6 Hz, 2H), 2.52 (m, 2H), 1.55 (m, 4H), 1.22 (d, J=7.1 Hz, 3H); $^{13}$C NMR (125 MHz, CDCl$_3$): δ 174.49, 148.45, 136.12 (t, J=23 Hz), 116.29 (quintet, J=22.6 Hz), 120.43, 119.78, 57.84, 53.33 (quintet, J=19.3 Hz), 52.55, 51.24, 50.15, 27.98, 27.07, 25.55, 14.85.

N,N-(4-(1-allyl-d$_5$-1H-1,2,3-triazol-4-yl)butyl)(allyl-D$_0$) L-alanine and N,N-(4-(1-allyl-d$_0$-1H-1,2,3-triazol-4-yl)butyl)(allyl-D$_5$) L-alanine 1.22 mmol of N,N-(4-(1-allyl-d$_5$-1H-1,2,3-triazol-4-yl)butyl)(allyl-D$_0$) L-alanine methyl ester (0.375 g) was charged to a 10 mL one neck flask with 2 mL of THF and 2 mL of 2M KOH and stirred at room temperature for 10 h. The reaction was monitored by TLC and ESI-MS until the starting material was completely consumed. Upon completion of the reaction, THF was removed by rotavap and the aqueous layer was neutralized by ~2 mL of 2M HCl. Water was then completely removed by rotavap and the residue was reconstituted by acetonitrile. Insoluble KCl salt was filtered and acetonitrile was removed by rotavap. The free acid of the alanine derivative, N,N-(4-(1-allyl-d$_5$-1H-1,2,3-triazol-4-yl)butyl)(allyl-D$_0$) L-alanine was recovered as a pale yellow greasy oil. Yield: quantitative. ESI-MS [M+H]$^+$=298.1 m/z; $^1$H NMR (500 MHz, DMSO-d$_6$): δ 10.62 (br, 1H), 7.90 (d, J=2.2 Hz, 1H), 6.05 (m, 1H), 5.53 (d, J=17.1 Hz, 1H), 5.45 (d, J=10.5

Hz, 1H), 4.18 (q, J=7.1 Hz, 1H), 3.83 (m, 2H), 3.15 (br, 2H), 2.64 (t, J=7.6 Hz, 2H), 1.69 (m, 4H), 1.52 (d, J=6.9 Hz, 3H).

N,N-(4-(1-allyl-$D_0$-1H-1,2,3-triazol-4-yl)butyl)(allyl-$D_5$) L-alanine methyl ester (0.247 g, 0.79 mmol) was used for hydrolysis by the same procedure described above and 0.230 g of N,N-(4-(1-allyl-$D_0$-1H-1,2,3-triazol-4-yl)butyl)(allyl-$d_5$) L-alanine (0.773 mmol) was obtained as a pale yellow gleasy oil. Yield: 97%. ESI-MS [M+H]$^+$=298.1 m/z; $^1$H NMR (500 MHz, DMSO-$d_6$): δ 10.54 (br, 1H), 7.89 (d, J=4.2 Hz, 1H), 6.03 (m, 1H), 5.25 (m, 1H), 5.16 (m, 1H), 4.98 (m, 2H), 4.18 (q, J=7.1 Hz, 1H), 3.15 (br, 2H), 2.64 (t, J=7.3 Hz, 2H), 1.69 (m, 4H), 1.52 (d, J=7.1 Hz, 3H).

N,N-(4-(1-allyl-$d_5$-1H-1,2,3-triazol-4-yl)butyl)(allyl-$D_0$) L-alanine N-hydroxysuccinimide ester and N,N-(4-(1-allyl-$d_0$-1H-1,2,3-triazol-4-yl)butyl)(allyl-$D_5$) L-alanine N-hydroxysuccinimide ester In a flame-baked 50 mL one neck flask, 2.75 g of N-hydroxysuccinimide was added to 14 mL of trifluoroacetic anhydride at room temperature under the stream of dry $N_2$ gas and the mixture was stirred for 4 h. The solvent was removed by rotavap and further eliminated by highvac overnight. The white crystal product, trifluoroacetic N-hydroxysuccinimide ester (TFA-NHS), was obtained, stored in the dry desiccator, and used just before activation of free acids.

In a flame-baked 50 mL one neck flask, 87 mg of N,N-(4-(1-allyl-$d_5$-1H-1,2,3-triazol-4-yl)butyl)(allyl-$D_0$) L-alanine (0.29 mmol) and 75 mg of TFA-NHS were added to 1 mL of dry DMF, and stirred overnight at room temperature. After the complete consumption of the starting material by monitoring TLC, the reaction mixture was separated by flash chromatography on silica gel (1:1=Hexane/EtOAc) and yielded 28 mg of N,N-(4-(1-allyl-$d_5$-1H-1,2,3-triazol-4-yl)butyl)(allyl-$D_0$) L-alanine N-hydroxysuccinimide ester (~0.7 mmol) as a yellow oil. Other purification methods such as crystallization would improve the overall yield. Yield: 24%. ESI-MS (100% acetonitrile for solvent) [M+H]$^+$=395.1 m/z. The stock solution of the heavy tag (169 m/z reporter ion) was prepared without further analysis by adding 20 μL dry DMSO to 1 mg of the NHS-ester product into each vials, and stored in −80° C. Each vial contains 1 mg of the reagent and used for each labeling experiment appropriately.

The same procedure was used for NHS ester activation of 52 mg of N,N-(4-(1-allyl-$D_0$-1H-1,2,3-triazol-4-yl)butyl)(allyl-$D_5$) L-alanine (0.175 mmol) and yielded 16 mg of the NHS-ester product. Yield: 23%. ESI-MS (100% acetonitrile for solvent) [M+H]$^+$=395.1 m/z. The stock solution vials of the light tag (164 m/z reporter ion) were prepared as described above and stored in −80° C.

EXAMPLE 2

Labeling of Peptides/Protein Digests with Isobaric Reagent Tags VIII and IX

50 μg of the model peptide, VIP (residue 1-12), HSDAVFTDNYTR in 50 μL of 100 mM $Na_2HPO_4$ was labeled with 5 μL of 5 μg/μL DMSO stock solution of light (VIII) and heavy (IX) tags, respectively, by incubating for 4 h at room temperature. The reaction was quenched by adding 50 μL, of 100 mM hydroxylamine and incubated for 7 h at room temperature to reverse unwanted by-products which contain isobaric reagent on tyrosine residues The mixture was acidified by adding 4 μL of formic acid and completely dried by speedvac. The residue was reconstituted by 100 μL 0.1% formic acid, desalted by the C18 desalting tip and eluted to 100 μL 0.1% formic acid 50% acetonitrile. The labeled VIP peptide eluent was properly diluted (~×20) by 0.1% formic acid 50% acetonitrile and analyzed by MALDI TOF, ESI-qTOF, and the LTQ-orbitrap with LC separation.

An aliquot of 1 μg of the protein digest was labeled with Reagent VIII and Reagent IX, respectively, and mixed with the 1:1 ratio, desalted, and injected into the nanoLC-LTQ-orbitrap instrument. 3 μg of Cullin1 digests were labeled with Reagent VIII and Reagent IX in a 1:2 ratio (Reagent VIII: Reagent IX). After conjugation, labeled Cullin1 digests were combined, desalted, and injected into the nanoLC-LTQ-orbitrap instrument.

EXAMPLE 3

Analysis of Peptides Labeled with Isobaric Reagent Tags of Formula VII and IX

Figure 7:
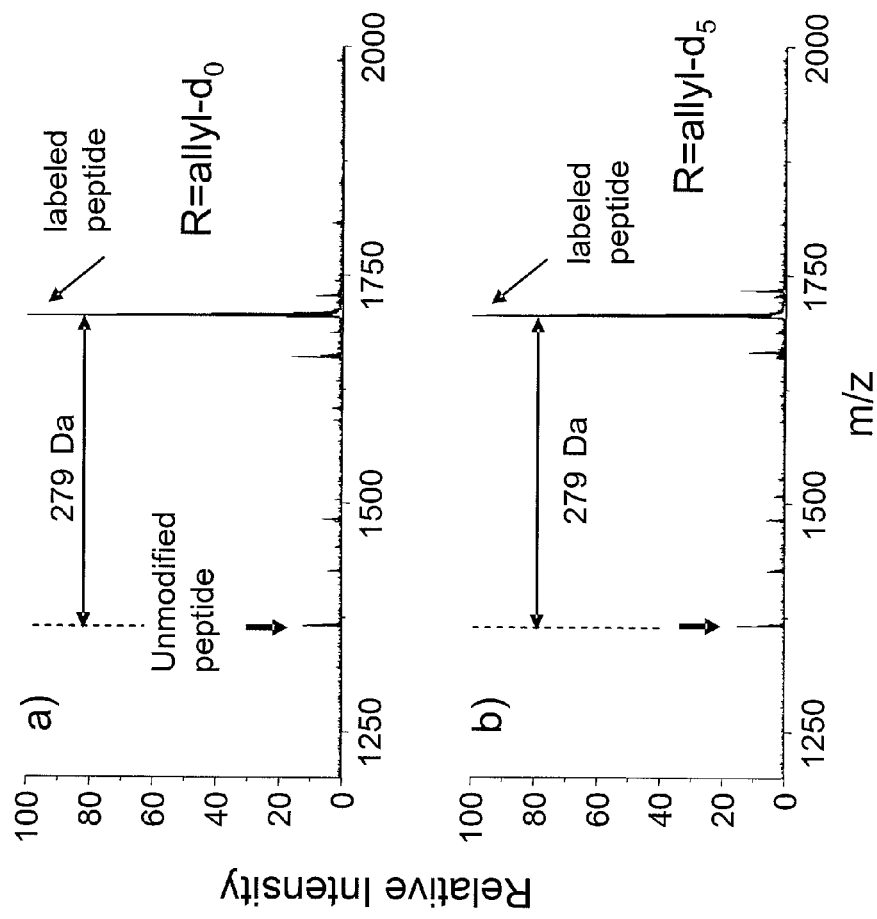
FIG. 7 shows spectra from MALDI TOF mass spectrometry analysis of peptide labeled with isobaric reagents of the present invention.

The masses of labeled peptides were increased by 279 Da as expected in MALDI TOF MS (FIG. 7). The labeling yields of Formula VIII (R=allyl-D0) (the light, L tag) and Formula IX (R=allyl-$d_5$) (the heavy, H tag) reagents were both ~90% estimated by the peak height comparison in the MALDI TOF MS spectra (FIG. 7). The exact masses of each labeled peptide were identical, and the labeled peptides appeared as one peak in all mass spectrometric analyses.

Figure 8:
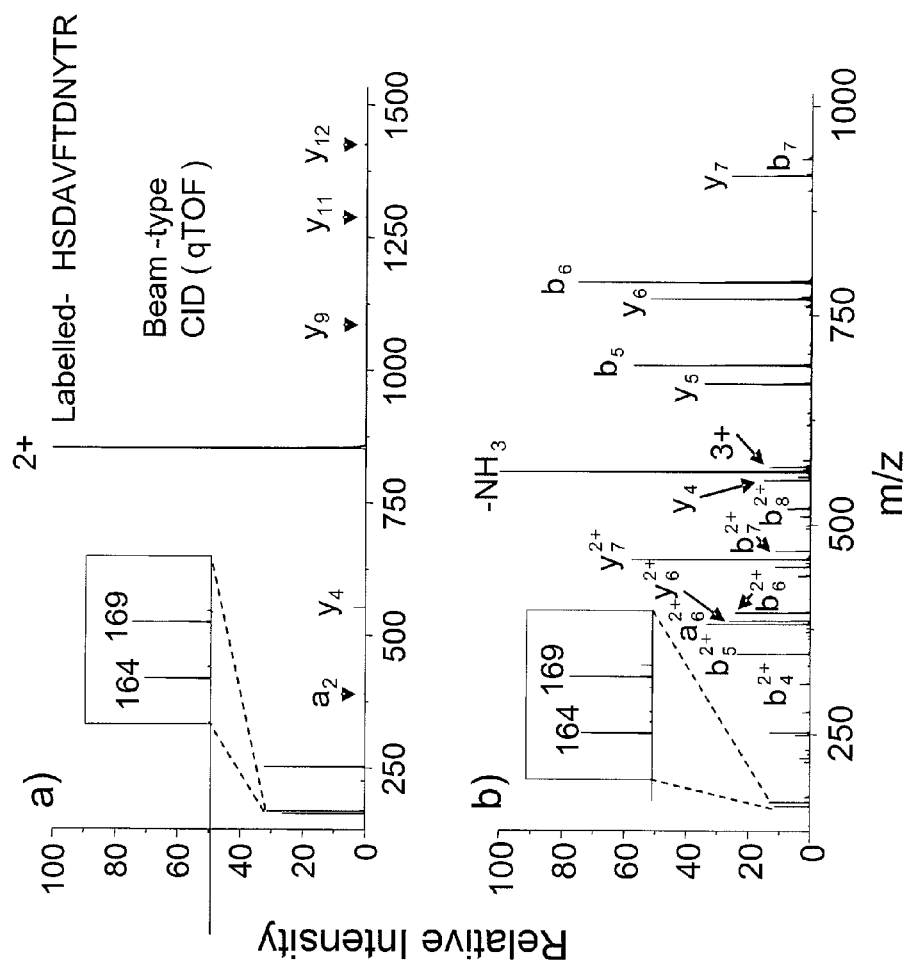
FIG. 8 shows spectra from beam-type CID of peptides labeled with isobaric reagents of the present invention.

Beam-type CID of the 2:3 mixture of labeled peptides in qTOF generated abundant reporter ions at 164.1 and 165.1 m/z as well as sequence ions, which confirmed the labeling site was the N-terminal amine (FIG. 8). The height ratio of reporter ions was estimated as expected in the triply charged case (H/L ($D_5$/$D_0$)=~1.5) (FIG. 8, panel b) but more deviation was observed in the doubly charged experiment (~1.26) (FIG. 8, panel a). The experimentally observed reporter ion ratios (D5: D0) were 1.26 for 2+ (doubly charged) and 1.499 for 3+ (triply charged) (theoretical 1.5).

Figure 9:
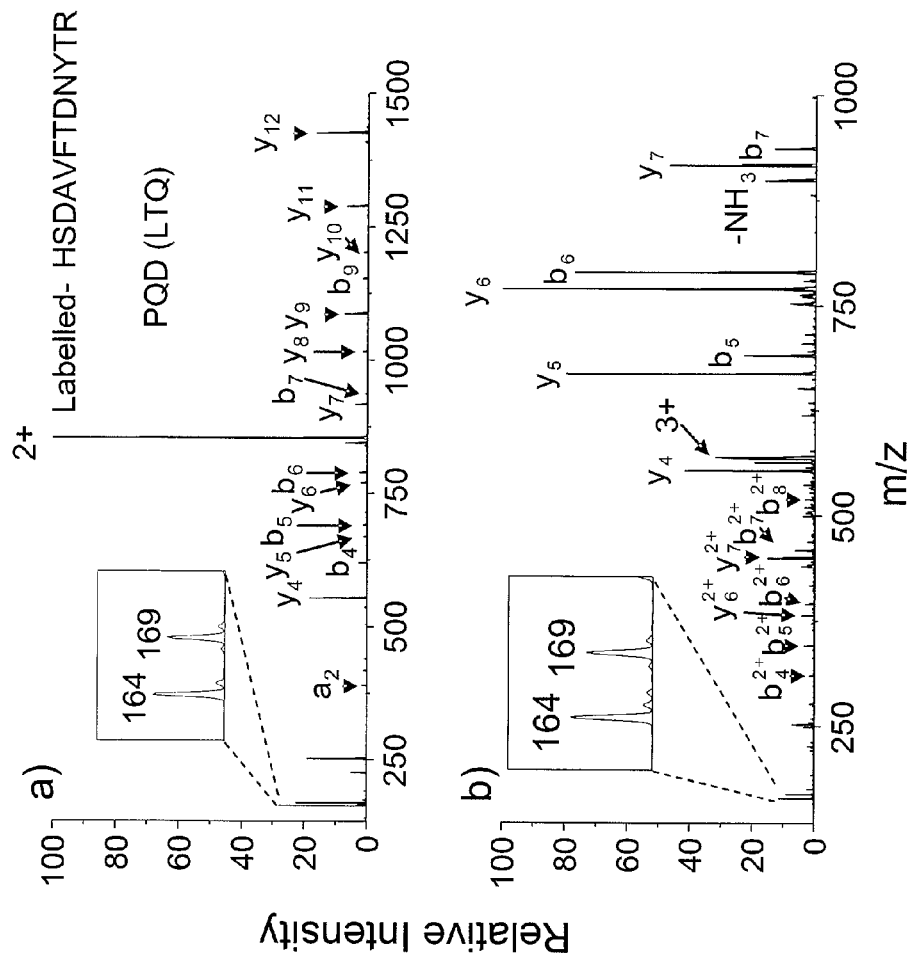
FIG. 9 shows spectra from PQD of peptides labeled with isobaric reagents of the present invention.
Figure 10A:
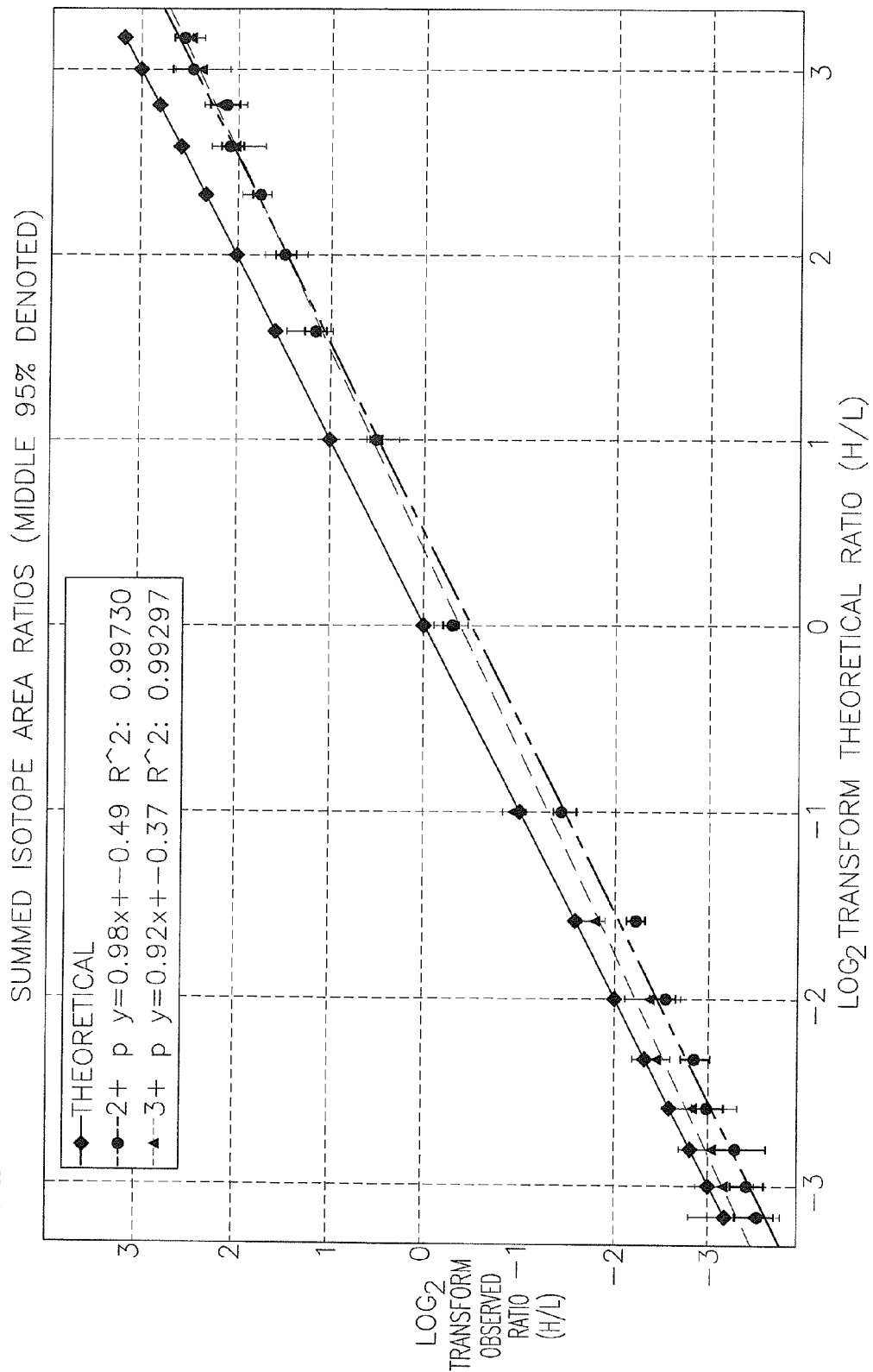
FIGS. 10a-10d show a graph of the linear dependency of the initial mixing ratios of peptides labeled with isobaric reagents of the present invention.
Figure 10B:
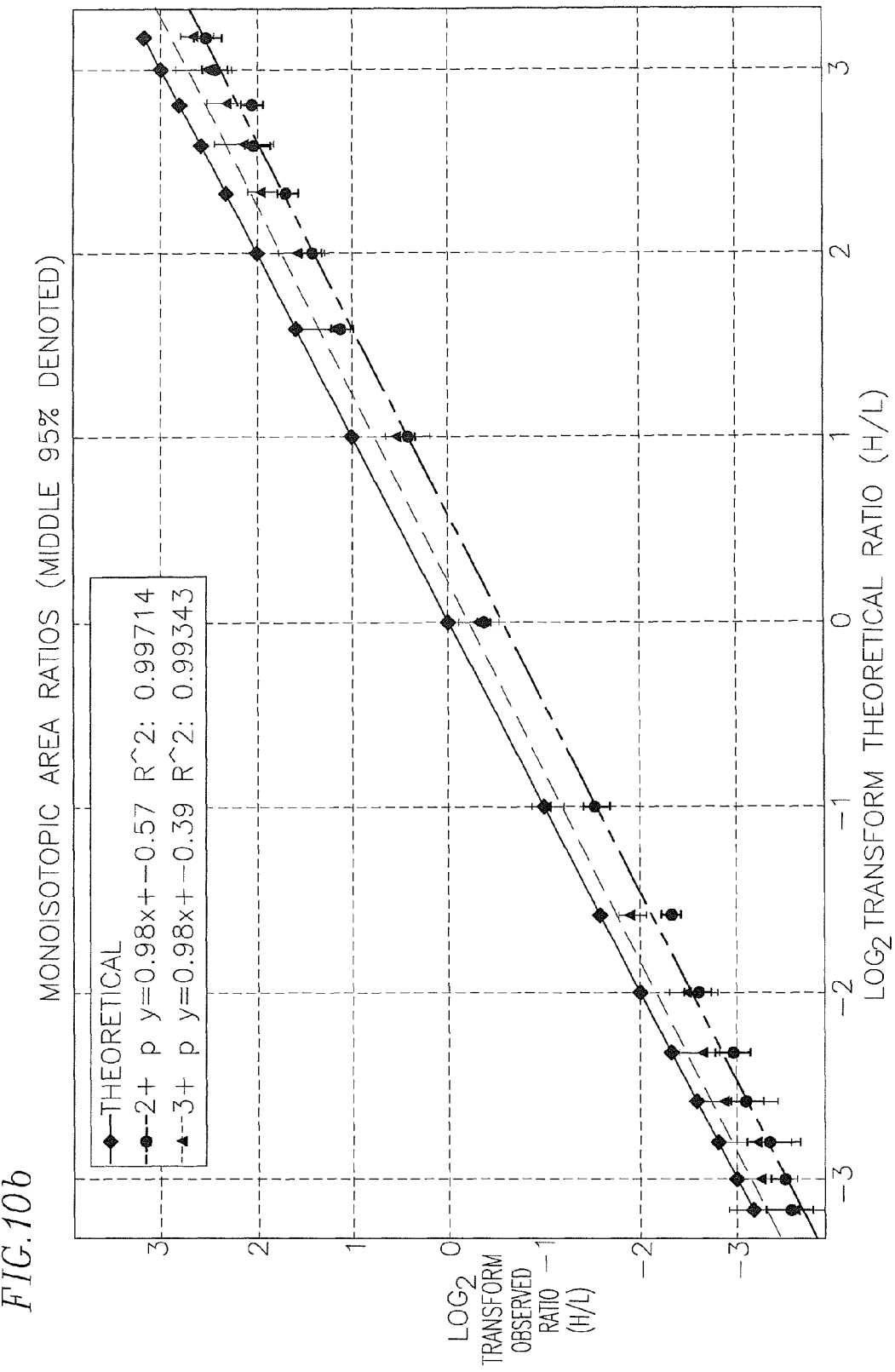
Figure 10C:
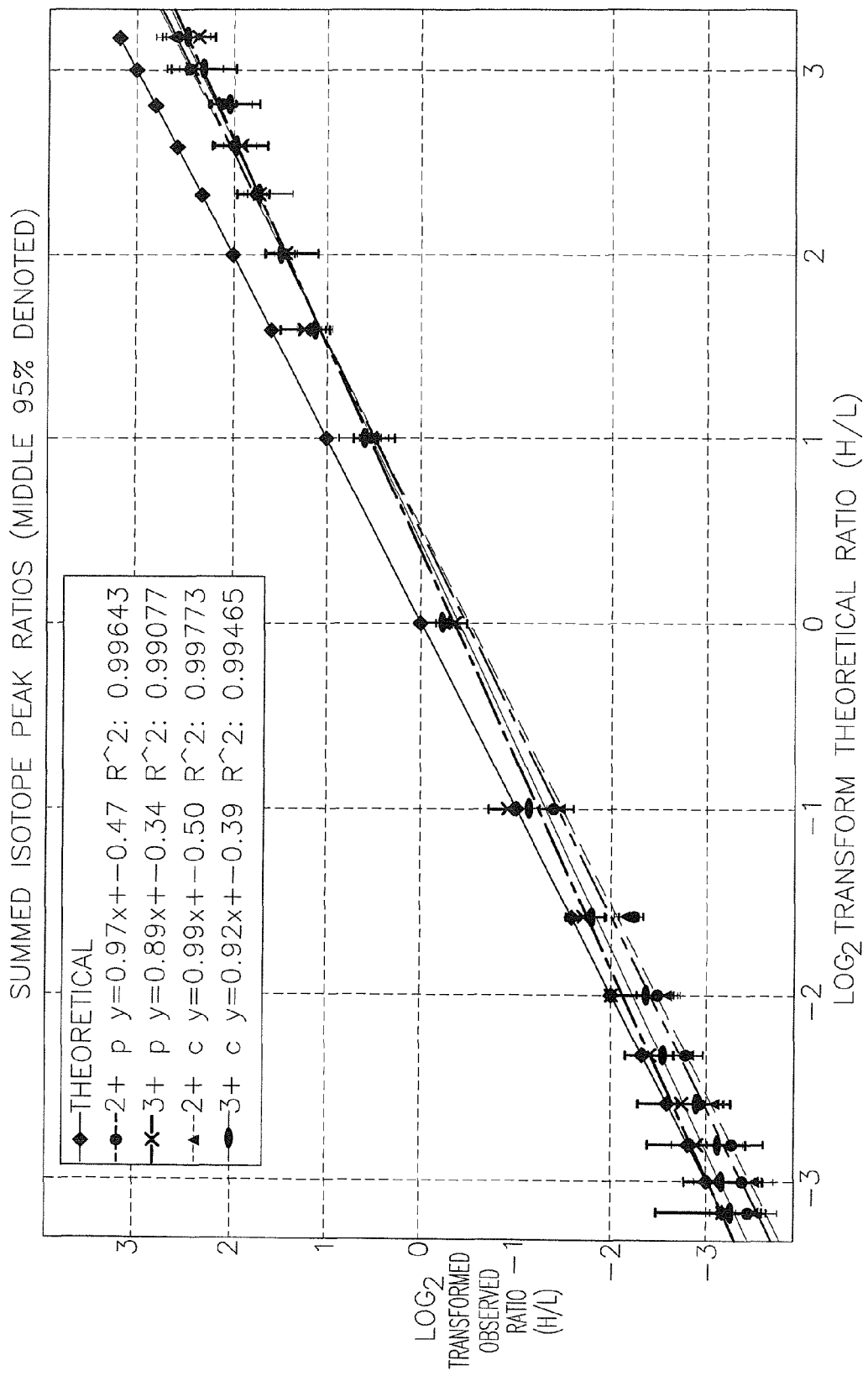
Figure 10D:
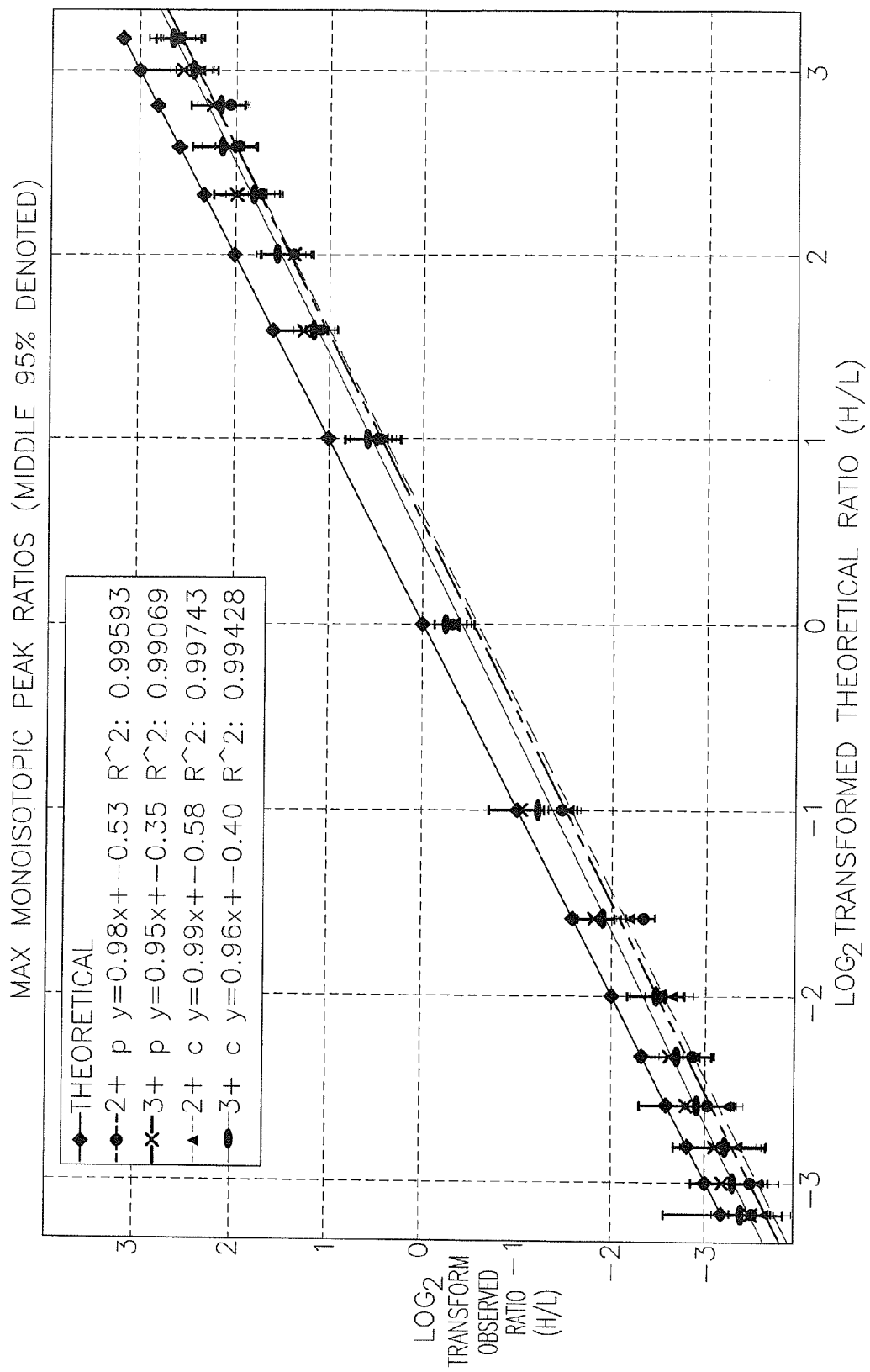

PQD of the 1:1 mixture of labeled peptides in the LTQ-orbitrap also produced abundant reporter ions, and the ratio was estimated as ~0.8 in both charge states (FIG. 9), which includes the initial experimental mixing error. That is, the experimentally observed reporter ion ratios (D5:D0) were 0.80 for 2+ and 0.81 for 3+, and it appears as the y-axis intercepts in the linear fitting lines in FIGS. 10a-10d. The overall linearity (slopes=~1.0) and quality of fitting ($R^2$=~0.99) are not affected by this error because it has well-defined systematic error sources.

A systematic study for testing the linear dependency on initial mixing ratio of labeled peptides toward the ratio of their reporter ions was performed using PQD in the LTQ-orbitrap by direct infusion. The PQD spectra of doubly and triply charged labeled peptides were recorded in profile and centroid modes and the intensities or areas of the reporter ions were used to plot the linear dependency on the initial mixing ratio (FIGS. 10a-10d, log 2-log 2 plot). The linear fitting trend lines obtained by calculating the log 2 of summations of: (FIG. 10a): the integration of all areas of isotopes in each reporter ions (164, 165, and 166 m/z for the light tag and 168, 169, 170, and 171 m/z for the heavy tag), FIG. 10b: the integration of only 164 and 169 m/z peak areas, FIG. 10c: peak heights of 164, 165, and 166 m/z for the light tag and 168, 169, 170, and 171 m/z for the heavy tag, and FIG. 10d: peak heights of only 164 and 169 m/z for y-axis and the log 2 of intended initial mixing ratios for x-axis. Relatively large (~0.4-0.5) y-axis intercepts in all figures are originated from systematic sources such as initial experimental mixing errors. Therefore, the overall linearity (slopes=~1.0) and quality of fitting ($R^2$=~0.99) are not affected.

All of the methods for data processing showed a good correlation ($R^2$~0.99) between the initial mixing ratio of labeled peptides. The systematic existence of the y-axis intercepts is attributed to the initial experimental mixing error.

Figure 11:
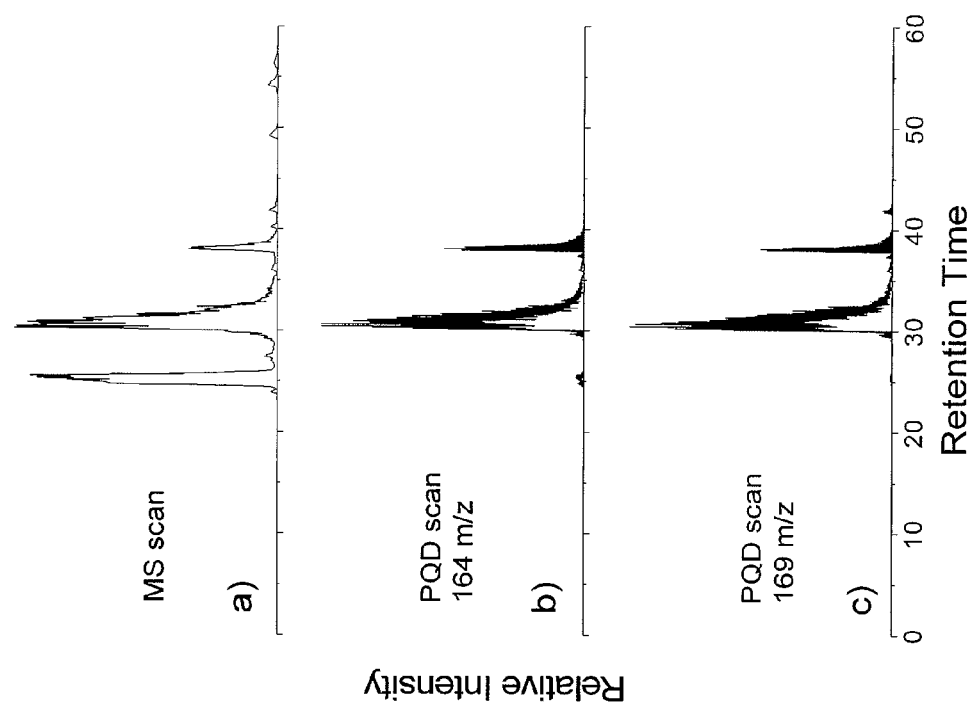
FIG. 11 shows nano-LC chromatograms of MS1 scan (a), and PQD scans (b, c) generated from peptides labeled with isobaric reagents of the present invention.

The retention times in nanoLC for both labeled peptides were measured using 2 μg amount of 1:1 mixture by monitoring 164 and 169 m/z ion current in PQD scans. As seen in FIG. 11, ion current diagrams for each of the reporter ions were identical along the LC separation. The base peaks in all chromatograms are related to labeled model peptides. Note that panel (b) and panel (c) are identical, indicating the same chromatographic property of D0- and D5-labeled peptides. The peak at 25 min in panel (a) is a non-labeled model peptide. The peaks appearing around 37 min in panel (b) and panel (c) are from labeled peptide fragments, AVFTDNYTR.

For protein model systems, simple protein digests constructed by the mixture of bovine serum albumin, ovalbumin, α and β caseins, and lysozyme were used for labeling with the initial mixing ratio for light (Formula VIII) and heavy (Formula IX) tags, 1:1. The nanoLC-LTQ-orbitrap results well reproduced the initial mixing ratio, and many peptides tagged by the reagents were used for overall quantification. Note that geometric standard deviations of mascot reported mixing ratios are relatively high. The same phenomenon was observed independently by the previous report in PQD of iTRAQ labeled peptides (Kocher, T. et al. *Journal of Proteome Research* 8, 4743-4752 (2009)).

Trypsin digests of Cullin1 protein complexes from the HEK293 cell line were labeled by light (Formula VIII) and heavy (Formula IX) reagents with the 1:2=L/H ratio. The combined sample was analyzed by PQD in the nanoLC-LTQ-orbitrap and the resulting LC-MS spectra were searched against the human IPI database (version 3.54) by mascot. The results generated by mascot search in the supporting information section summarize lists of identified proteins with the quantification ratios observed by calculating the ratio of 169 versus 164 m/z reporter ions. Although geometric standard deviation is relatively large due to the poor performance of PQD, the reported median numbers for quantification are close to 2 for all identified proteins.

EXAMPLE 4

Instruments Used

Matrix-assisted laser desorption/ionization time-of-flight (MALDI TOF) spectra were acquired using Voyager DE-Pro mass spectrometer (Applied Biosystems, Foster City, Calif.) in the reflectron mode with a 20 kV acceleration voltage, a 150 ns delay extraction time and a 75% grid voltage. A 0.5 μL sample of the derivatized peptide solution was mixed with 0.5 μL of 10 mg/mL CHCA matrix solution in 0.1% TFA, 50% ACN, and 50% $H_2O$ and the mixed spots were dried and introduced to the mass spectrometer for analyses. For all spectra, 100 shots were averaged.

Beam-type CID experiments were performed using Micromass Q-TOF ultra-2 (Waters, UK) in positive ion mode with the microelectrospray ion source. The samples were analyzed by a nanoflow HPLC, Proxeon easy-nLC-System (Proxeon Biosystems) coupled on-line via a nanoelectrospray ion source (Proxeon Biosystems) to a LTQ-Orbitrap mass spectrometer (Thermo Fisher Scientific). Samples were loaded onto a $C_{18}$-reversed phase column (15 cm long, 75 μm inner diameter, packed in-house with ReproSil-Pur $C_{18}$-AQ 3 μm resin in buffer A (5% ACN, 0.2% formic acid) with a flow rate of 500 nl/min for 24 min and eluted with a linear gradient from 0% to 36% buffer B (80% ACN 0.2% formic acid) over 110 minutes, followed by ten minutes at 100% buffer B, at a flow rate of 350 nl/min. The column was re-equilibrated with buffer A. Mass spectra were acquired in the positive ion mode applying data-dependent acquisition with automatic switching between survey scan and tandem mass spectrum acquisition. Samples were analyzed with a top 5 method; acquiring one orbitrap survey scan in the mass range of m/z 400-1600 followed by MS/MS of the five most intense ions in the LTQ in the mass range of m/z 100-1600. The target value in the LTQ-Orbitrap was 500,000 for survey scan at a resolution of 60,000 at m/z 400. Fragmentation in the LTQ was performed by Pulsed Q-Dissociation (PQD) with a target value of 5,000 ions. Selected sequenced ions were dynamically excluded for 30 s. General mass spectrometric conditions were: spray voltage, 2.4 kV; no sheath and auxiliary gas flow; ion transfer tube temperature, 200° C.; normalized collision energy (29%) using wide band activation mode for MS/MS. An activation of q=0.55 and delay time of 0.4 ms were applied in MS/MS acquisitions.[18]

EXAMPLE 5

Data Processing of Examples

The raw files from the LTQ-orbitrap mass spectrometer were converted to mascot generic format (MGF) files using ReAdW4Mascot (version 20090305a, available from the National Institute of Standards and Technology at http://peptide.nist.gov/software/ReAdW4Mascot2_20090305a.zip). PQD of the labeled VIP peptide acquired for testing of the linear dependency in reporter ion formation was then analyzed using in-house software and best-fit lines were calculated using linear regression. Error bars are displayed for the middle 95% reported ion ratios. For the Cullin1 pull-down search, a target sequence database was constructed from the human IPI database (version 3.54) and a small containment protein database. A decoy database was constructed from the target following the protocol in Cox and Mann (Cox, J. & Mann, M. *Nat. Biotechnol.* 26, 1367-1372 (2008)). The decoy database was then appended to the target and used to estimate the false discovery rate of the database search. The database search was performed using mascot (version 2.2.06, Matrix Science, http://www.matrixscience.com). The database search parameters were as follows: 0.5 Da fragment ion mass tolerance, 10 ppm precursor ion mass tolerance, trypsin enzyme specificity, up to two missed cleavages, fixed carbamidomethyl (57.02146 Da) modification of cysteine, variable modifications of oxidation (15.99491 Da) of methionine, carbamylation (43.005814 Da) of the N-terminal, and quantitation enabled. The mascot quantitation parameters were as follows: fixed the N-terminal modification of 279.210745 Da with reporter ions of 164.1188 and 169.1502 m/z. Reported mascot protein quantitation ratios were the median of the top scoring peptide reporter ion ratios, with at least one bold red peptide and two peptide ratios. Each peptide ratio must score at least as high as the homology threshold and outlier peptide ratios are discarded using the Mascot auto outlier detector. Reported proteins had a p-value<0.05.

The invention has been described with preferred and exemplary embodiments, but is not limited thereto. Other features and modifications will be apparent to the skilled person based on this disclosure. The invention is limited only by the appended claims and their equivalents.

What is claimed is:

1. A reagent for labeling an analyte, the reagent represented by Formula I:

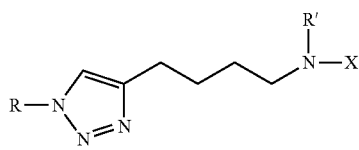

(I)

wherein:
R is a hydrocarbon group or a hydrocarbon group containing one or more heteroatoms;
R' is an isotopomer of R; and
X is a reactive group capable of coupling to the analyte.

2. The reagent of claim 1, wherein the one or more heteroatoms is oxygen.

3. The reagent of claim 1, wherein the one or more heteroatoms is nitrogen.

4. The reagent of claim 1, wherein X is selected from the group consisting of active esters, mixed anhydrides, and hydroxy reactive groups.

5. The reagent of claim 1, wherein X is a thiol group.

6. The reagent of claim 1, wherein the analyte is selected from the group consisting of proteins, peptides, nucleic acids, lipids, carbohydrates, steroids, and small molecules.

7. The reagent of claim 1, wherein at least one of R and R' is synthesized using isotopic substitution.

8. The reagent of claim 7, wherein the isotopic substitution includes at least one isotope selected from the group consisting of $^1H$, $^2H$, $^3H$, $^{12}C$, $^{13}C$, $^{14}C$, $^{14}N$, $^{15}N$, $^{16}O$, $^{17}O$, and $^{18}O$.

9. The reagent of claim 1, wherein the hydrocarbon group is selected from the group consisting of alkyl, alkenyl, alkynyl, cycloalkyl, cycloalkenyl, aryl, aralkyl, arylalkyl, alkaryl, ether, and hetero-substituted hydrocarbon groups.

10. The reagent of claim 1, wherein the hydrocarbon group is selected from the group consisting of methyl, ethyl, propyl, isopropyl, butyl, isobutyl, allyl, and benzyl.

11. The reagent of claim 1, wherein the hydrocarbon group is polyethylene glycol.

12. A method of detecting at least one analyte comprising:
forming a labeled analyte by labeling the at least one analyte with a reagent of claim 1;
separating the labeled analyte by chromatography;
ionizing the separated, labeled analyte to obtain an analyte ion;
isolating the analyte ion;
activating the isolated analyte ion to obtain a reporter ion; and
detecting the mass of the reporter ion by tandem mass spectrometry.

13. The method of claim 12, wherein the chromatography step comprises liquid chromatography-mass spectrometry (LC-MS); the ionizing step comprises matrix-assisted laser desorption ionization (MALDI), electrospray ionization (ESI), or fast atom bombardment (FAB); and the activating step comprises pulsed Q dissociation (PQD), collision induced dissociation (CID), higher energy C-trap dissociation (HCD), or CID-HCD.

14. A kit comprising (m) number of reagents for labeling (m) number of analytes, the kit comprising:
a first reagent; and
at least a second reagent, wherein the first reagent and the at least a second reagent are, independently represented by Formula I:

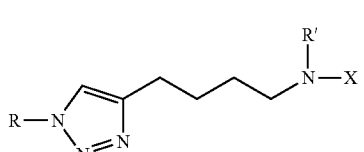

(I)

wherein:
R is a hydrocarbon group or a hydrocarbon group containing one or more heteroatoms;
R' is an isotopomer of R; and
X is a reactive group capable of coupling to the analytes,
wherein for each reagent, the sum of the mass of R and the mass of R' is constant, and wherein the mass of R of each reagent differs from the mass of every other R of the reagents in the kit, and the mass of R' of each reagent differs from the mass of every other R' of the reagents in the kit.

15. The kit of claim 14, wherein the one or more heteroatoms is oxygen.

16. The kit of claim 14, wherein the one or more heteroatoms is nitrogen.

17. The kit of claim 14, wherein X is selected from the group consisting of active esters, mixed anhydrides, and hydroxy reactive groups.

18. The kit of claim 14, wherein X is a thiol group.

19. The kit of claim 14, wherein the at least one analyte is selected from the group consisting of proteins, peptides, nucleic acids, lipids, carbohydrates, steroids, and small molecules.

20. The kit of claim 14, wherein at least one of R and R' is synthesized using isotopic substitution.

21. The kit of claim 20, wherein the isotopic substitution includes at least one isotope selected from the group consisting of $^1H$, $^2H$, $^3H$, $^{12}C$, $^{13}C$, $^{14}C$, $^{14}N$, $^{15}N$, $^{16}O$, $^{17}O$, and $^{18}O$.

22. The kit of claim 14, wherein the hydrocarbon group is selected from the group consisting of alkyl, alkenyl, alkynyl, cycloalkyl, cycloalkenyl, aryl, aralkyl, arylalkyl, alkaryl, ether, and hetero-substituted hydrocarbon groups.

23. The kit of claim 14, wherein the hydrocarbon group is selected from the group consisting of methyl, ethyl, propyl, isopropyl, butyl, isobutyl, allyl, and benzyl.

24. The kit of claim 14, wherein the hydrocarbon group is polyethylene glycol.

25. A method of detecting (m) number of analytes comprising:
forming (m) number of labeled analytes by labeling the (m) number of analytes with the kit comprising (m) number of reagents of claim 14;
separating the labeled analytes by chromatography;
ionizing the separated, labeled analytes to obtain analyte ions;
isolating the analyte ions;
activating the isolated analyte ions to obtain a reporter ions; and
detecting the mass of the reporter ions by tandem mass spectrometry.

26. A kit comprising (m) number of reagents for labeling (m) number of analytes, the kit comprising:
a first reagent; and
at least a second reagent, wherein the first reagent and the at least a second reagent are, independently represented by Formula X:

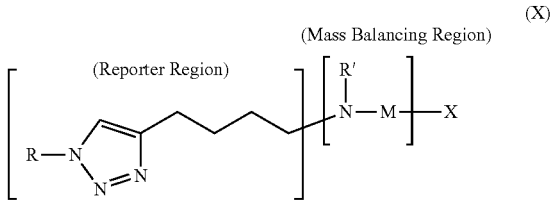

(X)

wherein:
R is a hydrocarbon group or a hydrocarbon group containing one or more heteroatoms;
R' is an isotopomer of R;
M is a hydrocarbon linker group; and
X is a reactive group capable of coupling to the analyte;
wherein for each reagent, the sum of the mass of the Reporter Region and the mass of Mass Balancing Region is constant, and wherein the mass of the Reporter Region of each reagent differs from the mass of every other Reporter Region of the reagents in the kit, and the mass of the Mass Balancing Region of each reagent differs from the mass of every other Mass Balancing Region of the reagents in the kit.

27. A method of detecting (m) number of analytes comprising:
forming (m) number of labeled analytes by labeling the (m) number of analytes with the kit comprising (m) number of reagents of claim 26;
separating the labeled analytes by chromatography;
ionizing the separated, labeled analytes to obtain analyte ions;
isolating the analyte ions;
activating the isolated analyte ions to obtain a reporter ions; and
detecting the mass of the reporter ions by tandem mass spectrometry.

* * * * *